United States Patent
Abdel-Malek et al.

(10) Patent No.: US 10,301,355 B2
(45) Date of Patent: May 28, 2019

(54) METHOD OF USING PHARMACEUTICAL COMPOSITIONS COMPRISING SELECTIVE PEPTIDE-BASED AGONISTS OF MELANOCORTIN 1 RECEPTOR

(71) Applicant: University of Cincinnati, Cincinnati, OH (US)

(72) Inventors: Zalfa A. Abdel-Malek, Cincinnati, OH (US); Leonid Koikov, Cincinnati, OH (US); James J. Knittel, Belchertown, MA (US)

(73) Assignee: University of Cincinnati, Cincinnati, OH (US)

( * ) Notice: Subject to any disclaimer, the term of this patent is extended or adjusted under 35 U.S.C. 154(b) by 28 days.

(21) Appl. No.: 15/794,301

(22) Filed: Oct. 26, 2017

(65) Prior Publication Data

US 2018/0066016 A1    Mar. 8, 2018

Related U.S. Application Data

(62) Division of application No. 14/646,410, filed as application No. PCT/US2013/071033 on Nov. 20, 2013, now Pat. No. 9,834,580.

(60) Provisional application No. 61/729,018, filed on Nov. 21, 2012.

(51) Int. Cl.

| | |
|---|---|
| *A61K 38/06* | (2006.01) |
| *A61K 38/07* | (2006.01) |
| *C07K 5/08* | (2006.01) |
| *C07K 5/10* | (2006.01) |
| *A61K 9/00* | (2006.01) |
| *C07K 5/117* | (2006.01) |
| *C07K 5/097* | (2006.01) |
| *A61K 8/64* | (2006.01) |
| *A61Q 19/00* | (2006.01) |
| *A61Q 19/04* | (2006.01) |
| *A61Q 19/08* | (2006.01) |
| *A61K 8/06* | (2006.01) |
| *A61Q 17/04* | (2006.01) |
| *A61K 38/00* | (2006.01) |

(52) U.S. Cl.
CPC .............. *C07K 5/1024* (2013.01); *A61K 8/06* (2013.01); *A61K 8/64* (2013.01); *A61K 9/0014* (2013.01); *A61K 38/06* (2013.01); *A61K 38/07* (2013.01); *A61Q 17/04* (2013.01); *A61Q 19/004* (2013.01); *A61Q 19/04* (2013.01); *A61Q 19/08* (2013.01); *C07K 5/0821* (2013.01); *A61K 38/00* (2013.01)

(58) Field of Classification Search
None
See application file for complete search history.

(56) References Cited

U.S. PATENT DOCUMENTS

| | | |
|---|---|---|
| 6,794,489 B2 | 9/2004 | Blood et al. |
| 7,745,408 B2 | 6/2010 | Humphrey |
| 8,440,793 B2 | 5/2013 | Perricone et al. |
| 2006/0003386 A1 | 1/2006 | Sharma et al. |
| 2011/0263508 A1 | 10/2011 | Kleinig et al. |

FOREIGN PATENT DOCUMENTS

WO   2011063366 A1   5/2011

OTHER PUBLICATIONS

Holder, J.R., Z. Xiang, R.M. Bauzo, and C. Haskell-Luevano, Structure-activity relationships of the melanocortin tetrapeptide Ac-His-D-Phe-Arg-Trp-NH2 at the mouse melanocortin receptors. 4. Modifications at the Trp position. Journal of Medicinal Chemistry, 2002. 45: p. 5736-5744.

Kennedy, C., J. ter Huume, M. Berkhout, N. Gruis, M. Bastiaens, W. Bergman, R. Willemze, and J.N. Bouwes Bavinck, Melanocortin 1 receptor (MC1R) gene variants are associated with an increased risk for cutaneous melanoma which is largely independent of skin type and hair color. Journal of Investigative Dermatology, 2001. 117: p. 294-300.

Epstein, J.H., Photocarcinogenesis, skin cancer and aging. Journal of the American Academy of Dermatology, 1983. 9: p. 487-502.

Pathak, M.A., Ultraviolet radiation and the development of non-melanoma and melanoma skin cancer: clinical and experimental evidence. Skin Pharmacol, 1991. 4 Suppl 1: p. 85-94.

Singh et al, "Incorporation of a bioactive reverse-turn heterocycle into a peptide template using solid-phase synthesis to probe melanocortin receptor selectivity and ligand confirmations by 2D 1H NMR," J. Med. Chem. 54: 1379-1390 (Feb. 9, 2011).

Catania, "Melanocortins: multiple actions and therapeutic potential," Advances in Experimental Medicine and Biology, vol. 681 (2010).

Koikov et al, "Analogs of sub-nanomolar hMC1R antagonist aK-184. An additional binding site within the human melanocortin receptor 1," Medicinal Chemistry Letters, 14: 3997-4000 (Jun. 9, 2004).

Y. Yang et al, "Novel binding motif of ACTH analogues at the melanocortin receptors," Biochemistry, Oct. 20, 2009, American Chemical Society, Inc., USA, vol. 48, No. 41, Oct. 20, 2009; pp. 9775-9784.

M. Chen et al, "Functional characterization of the modified melanocortin peptides responsible for ligand selectivity at the human melanocortin receptors," Peptides, Elsevier, Amsterdam, NL, vol. 27, No. 11, Nov. 1, 2006, pp. 2836-2845.

(Continued)

*Primary Examiner* — Kevin S Orwig
(74) *Attorney, Agent, or Firm* — Dinsmore & Shohl LLP

(57) ABSTRACT

Short tri- and tetrapeptides according to the following Formula I $Ar(CH_2)_m X^1 — X^2 — CO — X^3 — X^4 — X^5 -(Trp)_n - NX^6 R$ are potent, selective agonists of melanocortin 1 receptor (MC1R). Provided herein are pharmaceutical compositions including Formula I peptide agonists of MC1R and methods of treating skin diseases and disorders that include administering to an individual in need thereof a therapeutic amount of a Formula I peptide. The peptides, pharmaceutical compositions, and methods described herein are useful in the treatment of diseases and disorders that benefit from agonism of MC1R, including melanoma, basal cell carcinoma, squamous cell carcinoma, porphyria, polymorphous light eruption, vitiligo, and solar urticaria.

13 Claims, 9 Drawing Sheets

(56) References Cited

OTHER PUBLICATIONS

L. N. Koikov et al, "Sub-Nanomolar hMC1R Agonists by End-Capping of the Melanocortin Tetrapeptide His-D-Phe-Arg-Trp-NH2," Bioorganic & Medicinal Chemistry Letters, Pergamon, Amsterdam, NL, vol. 13, Jan. 1, 2003, pp. 2647-2650.
A. R. Ruwe et al, "Semi-rigid tripeptide agonists of melanocortin receptors," Bioorganic & Medicinal Chemistry Letters, Pergamon, Amsterdam, NL, Sep. 1, 2009, pp. 5176-5181.
Zalfa Abdel-Malek et al, "alpha-MSH tripeptide analogs activate the melanocortin 1 receptor and reduce UV-induced DNA damage in human melanocytes," Pigment Cell & Melanoma Research, vol. 22, No. 5, Oct. 2009, pp. 635-644.
Zalfa A. Abdel-Malek, "Development of α-Melanocortin Analogs for Melanoma Prevention and Targeting," Chapter 10, Melanocortins: Multiple Actions and Therapeutic Potential, edited by Anna Catania. 2010 Landes Bioscience and Springer Science & Business Media.
Zalfa A. Abdel-Malek et al, "Melanocortins and the melanocortin 1 receptor, moving transitionally towards melanoma prevention," Archives of Biochemistry and Biophysics 563 (2014) pp. 4-12.
Abdel-Malek, Z.A., A.L. Kadekaro, R.J. Kavanagh, A. Todorovic, L.N. Koikov, J.C. McNulty, P.J. Jackson, G.L. Milhauser, S. Schwemberger, G. Babcock, C. Haskell-Luevano, and J.J. Knittel, Melanoma prevention strategy based on using tetrapeptide alpha-MSH analogs that protect human melanocytes from UV-induced damage and cytotoxicity. Faseb J, 2006. 20: p. 1561-1563.
Mountjoy, K.G., L.S. Robbins, M.T. Mortrud, and R.D. Cone, The cloning of a family of genes that encode the melanocortin receptors. Science, 1992. 257: p. 1248-1251.
Abdel-Malek, Z., V.B. Swope, I. Suzuki, C. Akcali, M.D. Harriger, S.T. Boyce, K. Urabe, and V.J. Hearing, Mitogenic and melanogenic stimulation of normal human melanocytes by melanotropic peptides. Proceedings of the National Academy of Sciences of the United States of America, 1995. 92: p. 1789-1793.
Abdel-Malek, Z.A., Melanocortin receptors: their functions and regulation by physiological agonists and antagonists. Cell Mol Life Sci, 2001. 58(3): p. 434-41.
Zhang, L., W.H. Li, M. Anthonavage, A. Pappas, D. Rossetti, D. Cavender, M. Seiberg, and M. Eisinger, Melanocortin-5 receptor and sebogenesis. Eur J Pharmacol. 660(1): p. 202-6. 2011.
Dorr, R.T., R. Lines, N. Levine, C. Brooks, L. Xiang, V.J. Hruby, and M.E. Hadley, Evaluation of melanotan-II, a superpotent cyclic melanotropic peptide in a pilot phase-I clinical study. Life Sci, 1996. 58(20): p. 1777-84.
King, S.H., A.V. Mayorov, P. Balse-Srinivasan, V.J. Hruby, T.W. Vanderah, and H. Wessells, Melanocortin receptors, melanotropic peptides and penile erection. Curr Top Med Chem, 2007. 7(11): p. 1098-1106.
Pfaus, J.G., A. Shadiack, T. Van Soest, M. Tse, and P. Molinoff, Selective facilitation of sexual solicitation in the female rat by a melanocortin receptor agonist. Proc Natl Acad Sci U S A, 2004. 101(27): p. 10201-4.
Yang, Y., C. Dickinson, C. Haskell-Luevano, and I. Gantz, Molecular basis for the interaction of [Nle4,D-Phe7] melanocyte stimulating hormone with the human melanocortin-1 receptor. J Biol Chem, 1997. 272(37): P. 23000-10.
Haskell-Luevano, C., S. Hendrata, C. North, T.K. Sawyer, M.E. Hadley, V.J. Hruby, C. Dickinson, and I. Gantz, Discovery of prototype peptidomimetic agonists at the human melanocortin receptors MC1R and MC4R. Journal of Medicinal Chemistry, 1997. 40: p. 2133-2139.
Suzuki, I., R. Cone, S. Im, J. Nordlund, and Z. Abdel-Malek, Binding of melanotropic hormones to the melanocortin receptor MC1R on human melanocytes stimulates proliferation and melanogenesis. Endocrinology, 1996. 137: p. 1627-1633.
Kadekaro, A.L., S. Leachman, R.J. Kavanagh, V. Swope, P. Cassidy, D. Supp, M. Sartor, S. Schwemberger, G. Babcock, K. Wakamatsu, S. Ito, A. Koshoffer, R.E. Boissy, P. Manga, R.A. Sturm, and Z.A. Abdel-Malek, Melanocortin 1 receptor genotype: an important determinant of the damage response of melanocytes to ultraviolet radiation. Faseb J, 2010. 24(10): p. 3850-60.
Kadekaro, A.L. et al, "α-Melanocortin and endothelin-1 activate anti-apoptotic pathways and reduce DNA damage in human melanocytes," Cancer Res, 2005. 65: pp. 4292-4299.
Garcia-Borron, J.C., B.L. Sanchez-Laorden, and C. Jimenez-Cervantes, Melanocortin-1 receptor structure and functional regulation. Pigment Cell Res, 2005. 18(6): p. 393-410.
Palmer, J.S., D.L. Duffy, N.F. Box, J.F. Aitken, L.E. O'Gorman, A.C. Green, N.K. Hayward, N.G. Martin, and R.A. Sturm, Melanocortin-1 receptor polymorphisms and risk of melanoma: Is the association explained solely by pigmentation phenotype? American Journal of Human Genetics, 2000. 66: p. 176-186.
Scott, M.C., I. Suzuki, and Z.A. Abdel-Malek, Regulation of the human melanocortin 1 receptor expression in epidermal melanocytes by paracrine and endocrine factors, and by UV radiation. Pigment Cell Research, 2002. 15: p. 433-439.
Swope, V.B., J.A. Jameson, K.L. McFarland, D.M. Supp, W.E. Miller, D.W. McGraw, M.A. Patel, M.A. Nix, G.L. Millhauser, G.F. Babcock, and Z.A. Abdel-Malek, Defining MC1R Regulation in Human Melanocytes by Its Agonist alpha-Melanocortin and Antagonists Agouti Signaling Protein and beta-Defensin 3. J Invest Dermatol., 2012 epub ahead of print.
Levine, N., S.N. Sheftel, T. Eytan, R.T. Dorr, M.E. Hadley, J.C. Weinrach, G.A. Ertl, K. Toth, and V.J. Hruby, Induction of skin tanning by the subcutaneous administration of a potent synthetic melanotropin. JAMA, 1991. 266: p. 2730-2736.
Langan, E.A., Z. Nie, and L.E. Rhodes, Melanotropic peptides: more than just 'Barbie drugs' and 'sun-tan jabs'? Br J Dermatol. 163(3): p. 451-5. 2010.
Swope VB, Abdel-Malek, "Significance of the Melanocortin 1 and Endothelin B Receptors in Melanocyte Homeostasis and Prevention of Sun-Induced Genotoxicity," Frontiers in Genetics. Accepted for publication online, 2016.

METHOD OF USING PHARMACEUTICAL COMPOSITIONS COMPRISING SELECTIVE PEPTIDE-BASED AGONISTS OF MELANOCORTIN 1 RECEPTOR

RELATED APPLICATIONS

This application is a divisional of U.S. application Ser. No. 14/646,410, filed May 21, 2015, which is a 35 U.S.C. § 371 National Stage Application of PCT/US2013/071033, filed Nov. 20, 2013, which claims the benefit of U.S. Provisional Application No. 61/729,018, filed Nov. 21, 2012, each of which is hereby incorporated by reference in its entirety.

FEDERALLY SPONSORED RESEARCH OR DEVELOPMENT

This invention was made with Government support under R01CA114095awarded by the National Cancer Institute (NCI). The Government has certain rights in the invention.

FIELD OF THE INVENTION

The presently disclosed subject matter relates to the field of melanocortin 1 receptor (MC1R) agonists. Specifically, the present invention relates to pharmaceutical compositions comprising selective tri- and tetrapeptide agonists of MC1R useful in protecting skin from ultraviolet (UV) radiation exposure and methods of treating skin conditions that benefit from agonism of MC1R.

BACKGROUND OF THE INVENTION

The melanocortin 1 receptor (MC1R) belongs to the family of melanocortin receptors (subfamily of G-protein coupled receptors, or GPCRs) comprised of five members (MC1R-MC5R), each encoded by a different gene. These receptors vary widely in their expression and tissue distribution, with the MC3R and MC4R being neuronal receptors, the MC2R predominantly expressed by the adrenal gland, and the MC1R and MC5R expressed in the skin. Alpha-melanocyte stimulating hormone (alpha-MSH) is a common native agonist for MC1R, MC3R, MC4R, and MC5R.

MC1R is expressed on the cell surface of melanocytes, cells that reside in the upper layer of the skin. Melanocytes provide photoprotection by synthesizing the pigment melanin that reduces the penetration of UV radiation and scavenges reactive oxygen radicals. UV radiation is the main etiological factor for skin cancers, including melanoma. Malignant transformation of melanocytes results in melanoma, the deadliest form of skin cancer. Melanoma incidence rates in the United States have been increasing for at least 30 years. From 2005 to 2009, the incidence of melanoma in Caucasians increased at a rate of 2.8% annually. American Cancer Society Facts and Figures (2013).

MC1R agonists work to protect the skin in two ways, enhancing repair of DNA damage and stimulating production of melanin by melanocytes. Studies have previously shown that activation of MC1R by its native, non-selective peptide ligand alpha melanocortin stimulating hormone (α-MSH) increases melanin synthesis. Treatment (6h-8h) of human melanocytes with α-MSH up-regulates expression of the MC1R gene, thus enhancing response of melanocytes to melanocortins. Further studies have shown that α-MSH enhances repair of UV-induced DNA photoproducts, which is expected to reduce mutations and malignant transformation, and inhibits apoptosis, and hence increases survival of human melanocytes with undamaged DNA.

For compounds targeting the skin, selectivity for MC1R is of particular importance. MC5R, while also expressed in the skin, is expressed on the sebaceous glands; its activation leads to increased sebum production, which causes acne. Zhang, L., et al., *Melanocortin-5 receptor and sebogenesis*, *Eur. J. Pharmacol.* 660(1): 202-06 (2011). Equally important is selectivity for MC1R versus MC3R and MC4R; commercial development of the potent but non-selective synthetic α-MSH analog melanotan II (MT-II) for sunless tanning was restricted by its off-target effects that included sexual arousal and spontaneous erections lasting for 1-5 hours, nausea, grade II somnolence, fatigue, stretching, yawning, and loss of appetite caused by undesired activation of MC3R and MC4R, in addition to the desired activation of MC1R. Dorr, R. T., et al., *Evaluation of melanotan II, a superpoleni cyclic melanotropic peptide in a pilot phase-1 clinical study, Life Sci.* 58(20): 1777-84 (1996); King, S. H., et al., *Melanocortin receptors, melanotropic peptides and penile erections, Curr. Top. Med. Chem.* 7(11): 1098-1106 (2007); Pfaus, J. G., et al., *Selective facilitation of sexual solicitation in the female rat by a melanocortin receptor agonist, Proc. Nat'l. Acad. Sci. USA* 101(27): 10201-04 (2004); Yang, Y., et al., *Molecular basis for the interaction of [Nle4, D-Phe7]melanocyte stimulating hormone with the human melanocortin-1 receptor, J. Biol. Chem.* 272(37): 2300-10 (1997).

Given the invasiveness of melanoma tumors, the poor prognosis, and the lack of effective treatment options, a substantial need exists for the development of selective agonists of MC1R for protecting skin and treating melanoma and other skin disorders that benefit from agonism of MC1R.

SUMMARY OF THE INVENTION

Provided herein are pharmaceutical compositions comprising:
(a) an effective amount of a selective peptide agonist of melanocortin 1 receptor (MC1R) according to the formula:

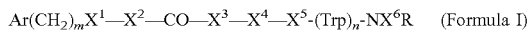

$$Ar(CH_2)_m X^1—X^2—CO—X^3—X^4—X^5-(Trp)_n-NX^6R \quad \text{(Formula I)}$$

or a pharmaceutically acceptable salt, solvate, or enantiomer thereof, wherein:

Ar is selected from the group consisting of unsubstituted or substituted phenyl and 5- or 6-membered heteroaryl;

m is 0, 1, 2, or 3;

$X^1$ is absent or $X^1$ is selected from the group consisting of O, NR', S, Se, and CR'R" wherein R' is selected from the group consisting of H, linear or branched C1-C4 alkyl, OH, and linear or branched C1-C4 O-alkyl and R" is selected from the group consisting of H and linear or branched C1-C4 alkyl; or wherein CR'R" is a C3-C6 cycloalkyl;

$X^2$ is absent or $X^2$ is selected from the group consisting of 1,2-phenylene, 1,3-phenylene, 1,4-phenylene, and CQ'Q" wherein Q' and Q" are each independently selected from the group consisting of H and linear or branched C1-C4 alkyl;

$X^3$ is selected from the group consisting of unsubstituted or substituted L-histidine (His), 3-(2-pyridyl)-L-alanine (2-PAL), 3-(3-pyridyl)-L-alanine (3-PAL), 3-(4-pyridyl)-L-alanine (4-PAL), 3-(2-thienyl)-L-alanine (2-Thi), 3-(3-thienyl)-L-alanine (3-Thi), 3-(2-furyl)-L-alanine (2-FurAla), 3-(3-furyl)-L-alanine (2-FurAla), L-homoserine (HoSer), O-methyl-L-homoserine (HoSer(Me)), and L-allylglycine;

$X^4$ is selected from the group consisting of unsubstituted or substituted D-phenylalanine (D-Phe), L-alpha-MePhe, 3-(2-thienyl)-D-alanine (D-2-Thi), 3-(3-thienyl)-D-alanine (D-3-Thi), 3-(2-furyl)-D-alanine (D-2-FurAla), and 3-(3-furyl)-D-alanine (D-3-FurAla);

$X^5$ is selected from the group consisting of unsubstituted or substituted L-arginine (Arg) and L-citrulline;

n is 0 or 1;

$X^6$ is selected from the group consisting of H, linear or branched C1-C4 alkyl, and C3-C4 cycloalkyl; and R is selected from the group consisting of H, linear or branched C1-C12 alkyl, linear or branched C1-C12 arylalkyl, and C3-05 cycloalkyl;

or wherein $X^6$ and R together form a C3-05 cycloalkyl; and (b) one or more pharmaceutically acceptable excipients.

Also provided herein are methods of treating a skin disorder comprising administering to an individual in need thereof a therapeutic amount of a Formula I MC1R agonist or pharmaceutical composition disclosed herein.

These and other objects, features, embodiments, and advantages will become apparent to those of ordinary skill in the art from a reading of the following detailed description and the appended claims.

DETAILED DESCRIPTION OF THE INVENTION

Figure 1:
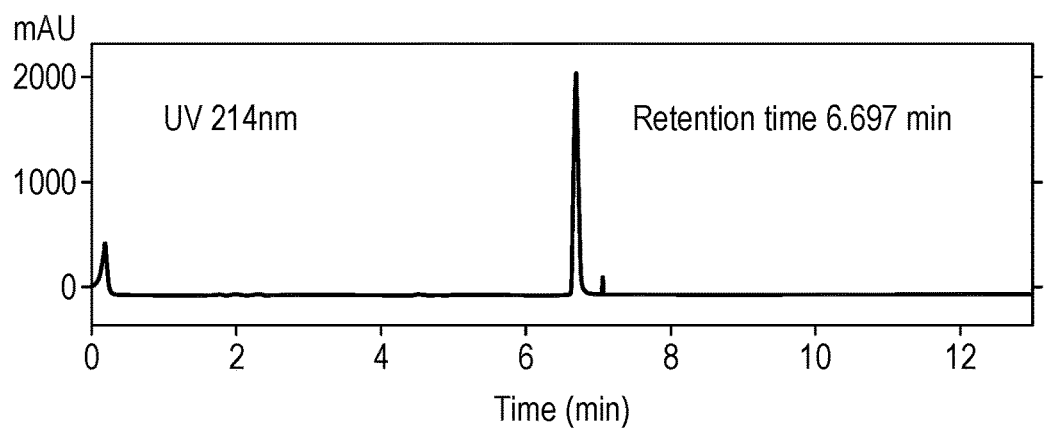
FIG. 1 shows HPLC data for LK-513 (Ph(CH$_2$)$_3$CO-His-(D-4-Bip)-Arg-NHMe) after 4 months storage at room temperature. Results indicate the peptide is highly stable and substantially free of degradation.
Figure 1:
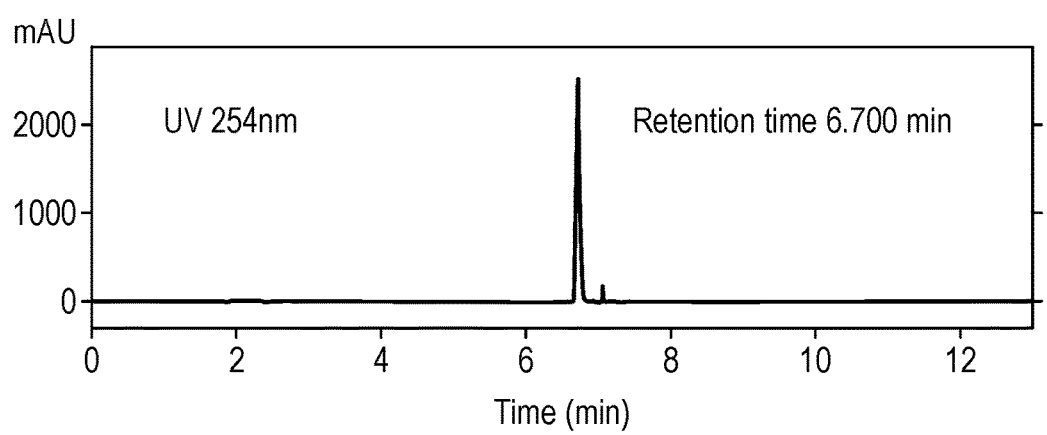
Figure 1:
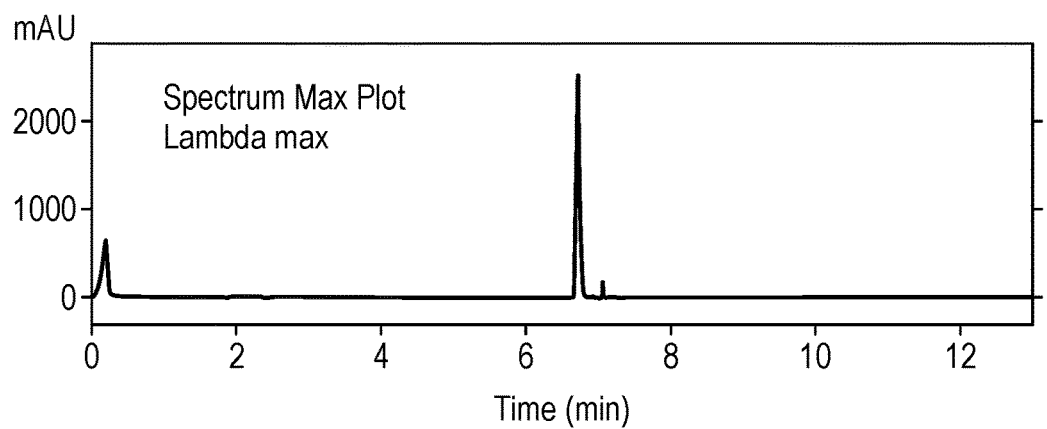

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the terms "treatment" or "treating" of a condition and/or a disease in an individual, including a human or lower mammal, means:

(i) preventing the condition or disease, that is, avoiding any clinical symptoms of the disease, particularly in individuals at risk for developing the condition or disease;

(ii) inhibiting the condition or disease, that is, arresting the development or progression of clinical symptoms; and/or (iii) relieving the condition or disease, that is, causing the regression of clinical symptoms.

Conditions and diseases treated include conditions and diseases associated with MC1R, particularly conditions and diseases that benefit from agonism of MC1R. In certain embodiments, conditions and diseases include inflammatory diseases and disorders. In other embodiments, conditions and diseases comprise skin disorders that include, but are not limited to, melanoma, basal cell carcinoma, squamous cell carcinoma, porphyria, polymorphous light eruption, vitiligo, and solar urticaria. In certain embodiments, the skin disorder is associated with a loss-of-function allelic variant of MC1R. In other embodiments, the skin disorder is associated with a mutation of a predisposition gene. In certain embodiments, the skin disorder is caused in part or exacerbated by exposure of skin melanocytes to UV light.

As used herein, the term "predisposition gene" refers to certain oncogenes and tumor suppressor genes that are causally associated with predisposition to cancer. Such mutations are inherited (germline mutations) or arise later in life (somatic). Various predisposition genes are known in the art and include, but are not limited to, p16, p14 ARF, and CDK4 and p53.

As used herein, the term "agonist" refers to an agent, such as a peptide, that triggers an agonist biological response when exposed to a receptor. In certain embodiments, peptides disclosed herein are agonists of the melanocortin 1 receptor (MC1R) and elicit an agonist response in MC1R that mimics the response of the endogenous MC1R ligand, alpha melanocortin stimulating hormone (α-MSH).

The stereochemistry of the standard amino acids is defined by two possible mirror image isomers or enantiomers. A natural amino acids occur in the L-stereoisomer form, with its mirror image D-stereoisomer rarely found in nature. The L- and D-amino acid convention is defined by matching amino acid structure to the structures of L-glyceraldehyde and D-glyceraldehyde. The asymmetric alpha-carbon of an amino acid is then aligned with the asymmetric second carbon of glyceraldehyde. Chemically similar groups in the structure are oriented similarly, namely, the amino acid alpha-carboxyl group (alpha-COO—) is aligned parallel to the aldehyde group (—CHO) of glyceraldehyde. The amino acid alpha-amino group (alpha-$NH_3$+) is aligned parallel to the hydroxyl group linked to the middle carbon of glyceraldehyde. Finally, the variable amino acid R-group is aligned with the methanol group of glyceraldehyde. In this configuration, the alpha-amino group of every L-amino acid is located on the left side and spatially above the alpha-carbon, as in the —OH group linked to the second asymmetric carbon of L-glyceraldehyde.

As used here, the terms "halo," "halide," or "halogen" refer to fluoro, chloro, bromo, and iodo groups.

As used herein, the term "aryl" as a group or part of a group refers to: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, haloalkyl, and the like.

As used herein, "heteroaryl" as a group or part of a group refers to an optionally substituted aromatic monocyclic or multicyclic organic moiety of about 5 to about 10 ring members in which one or more of the ring members is/are element(s) other than carbon, for example nitrogen, oxygen or sulphur. Examples of suitable optionally substituted heteroaryl groups include optionally substituted benzimidazolyl, furyl, imidazolyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups. Heteroaryl groups may be substituted with one or more heteroaryl group substituents which may be the same or different, where "heteroaryl group substituent" includes, for example acyl, acylamino, alkoxycarbonyl, alkylenedioxy, aroyl, aroylamino, aryl, arylalkyloxycarbonyl, aryloxycarbonyl, carboxy, cyano, halo, heteroaroyl, heteroaryl, heteroaroylamino, hydroxy, nitro, trifluoromethyl, and the like.

As used herein, "alkyl" means, unless otherwise specified, as a group or part of a group, an aliphatic hydrocarbon group which may be linear or branched having about 1 to about 12 carbon atoms (C1-C12) in the chain. In certain embodiments, alkyl groups have from 1 to about 6 carbon atoms (C1-C6). In a more specific embodiment, alkyl refers to linear or branched alkyl having about 1 to about 4 carbon atoms (C1-C4) in the chain. Exemplary alkyl groups include methyl, ethyl, n-propyl, i-propyl, n-butyl, i-butyl, s-butyl, t-butyl, n-pentyl, 3-pentyl, heptyl, octyl, nonyl, decyl, dodecyl, and the like.

As used herein, the term "cycloalkyl" refers to an optionally substituted non-aromatic monocyclic or multicyclic ring system of at least 3 carbon atoms. Particular monocyclic cycloalkyl rings include C3-7cycloalkyl such as cyclopropyl, cyclopentyl, cyclohexyl and cycloheptyl. Exemplary multicyclic cycloalkyl rings include perhydronaphthyl, adamant-(1- or 2-)yl and norbornyl and spirocyclic groups (e.g. spiro[4,4]non-2-yl). The cycloalkyl group may be substituted by one or more (e.g. 1, 2, or 3) substituents chosen from, for example, alkyl, aryl, arylalkyl, halo, halo substituted alkyl, hydroxyalkyl, hydroxy, alkoxy, and the like. In a specific embodiment, cycloalkyl refers to C3-C5 cycloalkyl.

As used herein, the term "alkoxy" refers to an alkyl-O— group in which the alkyl group is as described herein. Exemplary alkoxy groups include methoxy, ethoxy, n-propoxy, i-propoxy, n-butoxy, heptoxy, and the like.

As used herein, "arylalkyl" refers to an aryl-alkyl-group in which the aryl and alkyl moieties are as previously described. In certain embodiments, arylalkyl groups contain a C1-C12 alkyl moiety. Exemplary arylalkyl groups include benzyl, 2-phenethyl, naphthlenemethyl, and the like.

Unless otherwise constrained by the definition of the individual substituent, all the above substituents should be understood as being all optionally substituted.

Unless otherwise constrained by the definition of the individual substituent, the term "substituted" refers to groups substituted with from 1 to about 5 substituents independently selected from the group consisting of hydrogen, halo, cyano, hydroxy, alkoxy, thiol, carboxy, carbonyl, sulfonyl, linear or branched alkyl, cycloalkyl, heterocycloalkyl, acyl, alkene, alkyne, aryl, heteroaryl, amino, and the like, any of the above substituents optionally being further substituted.

As used herein, the term "sunscreen" refers to an agent applied to the skin to prevent sunburn by chemically blocking UV radiation from the sun. Many sunscreens are known in the art and include, but are not limited to, titanium dioxide, zinc oxide, PABA esters (glyceryl, padimate A and padimate O), salicylates (homosalate, octyl salicylate), cinnamates (cinoxate, octyl methoxycinnamate, octocrylene), benzophenones, ecamsule (Mexoryl™), and the like.

As used herein, the terms "therapeutic amount" and "effective amount" refer to the quantity of a composition or agent which is sufficient to effect a desired therapeutic response without undue adverse side effects (such as toxicity, irritation, or allergic response) commensurate with a reasonable benefit/risk ratio when used in the manner of this disclosure. The specific therapeutic amount will vary with such factors as the particular condition being treated, the physical condition of the individual being treated, the duration of the treatment, the nature of concurrent therapy (if any), and the specific formulations employed and the structure of the agent or its derivatives.

MC1R Agonists

Small peptide agonists according to the following formula are surprisingly potent and selective agonists of MC1R:

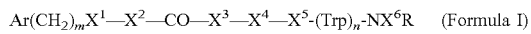

$$Ar(CH_2)_m X^1 - X^2 - CO - X^3 - X^4 - X^5 -(Trp)_n - NX^6 R \quad \text{(Formula I)}$$

or a pharmaceutically acceptable salt, solvate, or enantiomer thereof.

In certain embodiments, Ar is selected from phenyl or 5- or 6-membered heteroaryl, any of which are optionally further substituted. In a specific embodiment, Ar is phenyl or substituted phenyl. In another specific embodiment, Ar is phenyl substituted with 1 to 5 substituents, each independently selected from the group consisting of halo, CN, OH, alkyl, cycloalkyl, haloalkyl, acyl, alkene, alkyne, alkoxy, aryl, heteroaryl, COY, COOY, SOY, SO$_2$Y', and SO$_2$NYY', wherein Y and Y' are each independently selected from H, alkyl, cycloalkyl, acyl, alkene, and alkyne, or wherein to X can optionally join to form a carbocyclic ring or a heterocyclic ring that is fused to Ar. In a very specific embodiment, Ar is selected from the group consisting of phenyl, and phenyl substituted with halo, alkyl, alkoxy, and OH.

In certain embodiments, m is 0, 1, 2, or 3. In a specific embodiment, m is 1 or 3, such that the peptide of Formula I contains a CH$_2$ or (CH$_2$)$_3$ moiety.

In another embodiment, $X^1$ is absent or $X^1$ is selected from the group consisting of O, NR', S, Se, and CR'R'' wherein R' is selected from the group consisting of H, linear or branched C1-C4 alkyl, OH, and linear or branched C1-C4 O-alkyl and R'' is selected from the group consisting of H and linear or branched C1-C4 alkyl; or wherein CR'R'' is a C3-C6 cycloalkyl.

In another embodiment, $X^2$ is absent or $X^2$ is selected from the group consisting of 1,2-phenylene, 1,3-phenylene, 1,4-phenylene, and CQ'Q'' wherein Q' and Q'' are each independently selected from the group consisting of II and linear or branched C1-C4 alkyl.

In certain embodiments, $X^3$ is selected from the group consisting of unsubstituted or substituted L-histidine (His), 3-(2-pyridyl)-L-alanine (2-PAL), 3-(3-pyridyl)-L-alanine (3-PAL), 3-(4-pyridyl)-L-alanine (4-PAL), 3-(2-thienyl)-L-alanine (2-Thi), 3-(3-thienyl)-L-alanine (3-Thi), 3-(2-furyl)-L-alanine (2-FurAla), 3-(3-furyl)-L-alanine (2-FurAla), L-homoserine (HoSer), O-methyl-L-homoserine (HoSer (Me)), and L-allylglycine. In a specific embodiment, $X^3$ is L-Histidine (His).

In certain embodiments, $X^4$ is selected from the group consisting of unsubstituted or substituted D-phenylalanine (D-Phe) or a bulky hydrophobic analog of D-Phe. While not desiring to be bound by theory, it is believed that bulky aromatic rings of certain substituted D-Phe moieties (e.g., D-4-tBuPhe, D-4-Bip, D-1-Nal, D-2-Nal, and the like) provide favorable interaction with a hydrophobic pocket of MC1R and prevent peptides of Formula I from binding with MC3R, MC4R, or MC5R. Further, the bulk and hydrophobicity of the $X^4$ moiety shield the polar amid bonds of peptides of Formula I from chemical and enzymatic degradation. Moreover, when $X^4$ comprises an amino acid in the D configuration, tripeptides of Formula I have no amide bonds with natural amino acids, and tetrapeptides of Formula I have only one amide bond between natural amino acids ($X^5$-Trp). While not desiring to be bound by theory, it is believed that the absence or reduction of amide bonds between natural amino acids further protect peptides of Formula I from chemical and enzymatic hydrolysis.

Accordingly, in certain embodiments, $X^4$ is selected the group consisting of unsubstituted or substituted D-Phe, L-alpha-MePhe, 3-(2-thienyl)-D-alanine (D-2-Thi), 3-(3-thienyl)-D-alanine (D-3-Thi), 3-(2-furyl)-D-alanine (D-2-FurAla), and 3-(3-furyl)-D-alanine (D-3-FurAla). In certain embodiments, substituted D-Phe comprises D-4-t-Bu-phenylalanine (D-4-tBuPhe), D-alpha-methylphenylalanine (D-alpha-MePhe), D-4-biphenylalanine (D-4-Bip), D-1-naphthylalanine (D-1-Nal), D-2-naphthylalanine (D-2-Nal), 4-FPhe, 4-ClPhe, 4-BrPhe, 4-IPhe, 4-NO$_2$Phe, or 3-NO$_2$Phe. In a specific embodiment, $X^4$ is selected from the group consisting of D-Phe, D-2-Thi, D-3-Thi, D-4-tBuPhe, D-alpha-MePhe, L-alpha-MePhe, D-4-Bip, D-1-Nal, and D-2-Nal. In a more specific embodiment, $X^4$ is selected from the group consisting of D-Phe, D-4-tBuPhe, D-4-Bip, D-1-Nal, and D-2-Nal. In a more specific embodiment, $X^4$ is selected from the group consisting of D-4-tBuPhe, D-4-Bip, D-1-Nal, and D-2-Nal. In certain embodiments, $X^4$ is in the D stereoisomer configuration.

In some embodiments, $X^5$ is selected from the group consisting of unsubstituted or substituted L-arginine (Arg) and L-citrulline. In a specific embodiment, $X^5$ is L-Arginine (Arg).

Formula I peptides comprise both tri- and tetrapeptides. In certain embodiments, the peptides of Formula I are tripeptides, wherein Trp is absent and n is 0. In other embodiments, the peptides of Formula I are tetrapeptides, wherein Trp is present and n is 1.

In certain embodiments, $X^6$ is selected from the group consisting of H, linear or branched C1-C4 alkyl, and C3-C4 cycloalkyl. In a specific embodiment, $X^6$ is selected from the group consisting of H and linear or branched C1-C3 alkyl. In a more specific embodiment, $X^6$ is selected from the group consisting of H, methyl, and ethyl.

In another embodiment, R is selected from the group consisting of H, linear or branched C1-C12 alkyl, linear or branched C1-C12 arylalkyl, and C3-05 cycloalkyl. In a specific embodiment, R is selected from the group consisting of H and linear or branched C1-C3 alkyl. In a more specific embodiment, R is selected from the group consisting of H, methyl, and ethyl.

Alternatively, in some embodiments $X^6$ and R taken together form a C3-C5 cycloalkyl.

In another embodiment, MC1R agonist peptides are provided according to the following formula:

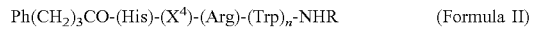

$$Ph(CH_2)_3 CO\text{-}(His)\text{-}(X^4)\text{-}(Arg)\text{-}(Trp)_n\text{-}NHR \quad \text{(Formula II)}$$

or a pharmaceutically acceptable salt, solvate, or enantiomer thereof, wherein:

Ph is unsubstituted or substituted phenyl;

$X^4$ is selected from the group consisting of D-phenylalanine (D-Phe), D-1-naphthylalanine (D-1-Nal), D-4-biphenylalanine (D-4-Bip), and D-4-t-butylphenylalanine (D-4-tBuPhe);

n is 0 or 1; and

R is selected from the group consisting of H, methyl, and ethyl.

In certain embodiments, R is methyl or ethyl when $X^4$ is D-Phe.

In a specific embodiment, MC1R agonists are selected from the peptides provided in Table 2, below. In a very specific embodiment, MC1R agonists are selected from the group consisting of Ph(CH$_2$)$_3$CO-His-(D-Phe)-Arg-Trp-NHEt (LK-487), Ph(CH$_2$)$_3$CO-His-(D-1-Nal)-Arg-Trp-NH$_2$ (LK-467), Ph(CH$_2$)$_3$CO-His-(D-4-Bip)-Arg-NH$_2$ (LK-511), Ph(CH$_2$)$_3$CO-His-(D-4-Bip)-Arg-NHMe (LK-513), and Ph(CH$_2$)$_3$CO-His-(D-4-tBuPhe)-Arg-NH$_2$ (LK-514).

In another embodiment, the peptides of Formula I and Formula II are tripeptides that lack tryptophan (Trp), such that n=0. Surprisingly, it has been found that short Formula I and Formula II tripeptides lacking Trp are particularly selective for MC1R over other melanocortin receptors. Without being bound by theory, it is believed that the presence of Trp may be a factor in agonism of MC3R, MC4R, and MC5R, but may not be as critical for agonism of MC1R. Hence, removal of the Trp moiety may yield short tripeptide agonists of MC1 R that avoid agonism of MC3R, MC4R, and MC5R, which has significant clinical implications.

Synthesis

Formula I and Formula II peptides disclosed herein are synthesized using solid-phase synthesis and Fmoc chemistry on Rink amide resin for unsubstituted amide peptides and alkyl indole resin for alkyl amide peptides (R=Me or Et) in dichloromethane, dimethylformamide (DMF) or N-methylpiperidone (NMP). The Fmoc groups are removed by piperidine solutions, benzotriazol-1-yloxy)tris(dimethylamino) phosphonium hexafluorophosphate or tetrafluoroborate (BOP) or O-benzotriazole-N,N,N',N'-tetramethyl-uronium-hexafluorophosphate (HBTU) are used as coupling agents and N-methylmorpholine (NMM) or N,N-diisopropylethylamine (DIPEA) as bases with optional addition of N-hydroxybenzotriazole (NHOBT). The crude peptides are cleaved from the resin with simultaneous deprotection with 95% trifluoroacetic acid (TFA)+triisopropyl silane (TIS) or 2-mercaptoethanol. Preparative HPLC (detection at 254 nm) is performed on 250×50 mm 10 μm Polaris C18-A column with 40 min gradient from 6 to 60% MeCN in water with 0.1% TFA at 60 mL/min. Analytical HPLC (detection at 214 and 254 nm) is performed at 1 mL/min on Altex 5 μm C18 column, 4.6×250 mm, 13 min gradient from 5 to 95% MeCN in water with 0.1% H$_3$PO$_4$. Identity of synthesized peptides is confirmed by mass spectrometry (MS).

Tri- and Tetrapeptide Secondary Structure

Natural agonists of melanocortin receptors, including alpha-, beta-, and gamma-melanocyte stimulating hormones, share the common melanocortin core sequence His$^6$-Phe$^7$-Arg$^8$-Trp$^9$ (HFRW), existing in a beta-turn conformation. Introduction of D-Phe$^7$ (HfRW) into the core sequence is believed to stabilize the beta-turn conformation in certain synthetic MSH analogs (NDP-MSH, MT-II), which increases potency. However, despite increased potency, the natural ligands and those analogs lack selectivity for MC1R.

Surprisingly, it has been found that rigidifying the peptide backbone of tri- and tetrapeptides disclosed herein by introducing beta-turn inducing amino acids leads to decreased activity of the peptides. Satyanarayanajois S. D., et al., *Conformations of end-capped melanocortin agonists RCO-X-Z-Arg-Trp-NH$_2$ by 2D-NMR, CD and computations, Peptides Breaking Away: Proceedings of the Twenty-First American Peptide Association* 384 (2009). Further, "soft fixation" of the tripeptide trans-4-HOC$_6$H$_4$CH=CHCO-His-D-Phe-Arg-NH$_2$ conformation without restricting dihedral angles of the backbone or side chains resulted in a compound with moderately increased MC1R selectivity and potency at mouse MCRs compared to the tripeptide LK-394. Ruwe A. R. et al., *Semi-rigid tripeptide agonists of melanocortin receptors, Bioorg. Med. Chem. Lett.* 19(17): 5176-81 (2009). However, this peptide proved to be less potent in human melanocytes. Thus, while not desiring to be bound by theory, it is believed that the conformational restraints favorable for longer peptides may be unfavorable for shorter MC1R agonists, including the Formula I and Formula II peptides disclosed herein.

Thus, in certain embodiments, it is desirable to select tri- and tetrapeptide agonists according to the formulas set forth herein that are substantially free from conformational restraints imposed by secondary peptide structure. That is, in certain embodiments, peptide agonists having a conformationally flexible structure (i.e., not constrained by a beta-turn or any rigid conformation) show increased potency, binding activity, and selectivity for MC1R.

Pharmaceutical Compositions

Provided herein are pharmaceutical compositions comprising Formula I and Formula II peptides disclosed herein, or combinations thereof. Pharmaceutical compositions as set forth herein may be provided in a variety of forms suitable for administration via topical or systemic routes. For example, systemic routes of administration include, but are not limited to, oral, intravenous, subcutaneous, intramuscular, intraperitoneal, sublingual, rectal, nasal, pulmonary, and transdermal administration.

In one embodiment, the pharmaceutical composition is an oral dosage form. Examples of suitable oral dosage forms include tablets, lozenges, aqueous or oily suspensions, dispersible powders or granules, emulsions, hard or soft capsules, syrups or elixirs. Compositions intended for oral use may be prepared according to any method known in the art for the manufacture of pharmaceutical compositions and such compositions may contain one or more excipients. Such compositions my be coated by conventional methods, typically with pH or time-dependent coatings, such that the active ingredient is released in the gastrointestinal tract in the vicinity of the desired application, or at various times to extend the desired action. Suitable coatings include, but are not limited to, one or more of cellulose acetate phthalate, polyvinylacetate phthalate, hydroxypropyl methyl cellulose phthalate, ethyl cellulose, Eudragit® coatings, waxes and shellac.

Other suitable dosage forms include suspensions or solutions suitable for intravenous, subcutaneous, intramuscular, intraperitoneal, sublingual, rectal, or nasal delivery.

In another embodiment, the pharmaceutical composition is a topical preparation for administration to the skin of an individual in need thereof. Suitable topical preparations may be in the form of a viscous liquid, solution, suspension, liposomal formulation, gel, jelly, cream, lotion, ointment, foam, spray, aerosol spray, aqueous or oily suspensions or solution, emulsion, or emulsion ointment. Topical formulation for application to skin may include ointments, lotions, pastes, creams, gels, drops, suppositories, sprays, liquids, powders, shampoos, and topical or transdermal patches.

Pharmaceutical compositions disclosed herein contain one or more pharmaceutically acceptable excipients. The term "excipient," as used herein, refers to any inactive substance incorporated into a pharmaceutical composition as a carrier for an active pharmaceutical ingredient. In one embodiment, the one or more pharmaceutically acceptable excipient is selected from the group consisting of polymers, resins, plasticizers, fillers, lubricants, diluents, solvents, co-solvents, suspending agents, buffer systems, surfactants, preservatives, sweetening agents, flavoring agents, pharmaceutical grade dyes or pigments, viscosity agents (thickeners), protein stabilizers, preservatives, and the like, and combinations thereof. Suitable pharmaceutical excipients are well-known in the art. See, for example, *Handbook of Pharmaceutical Excipients, Sixth Edition*, edited by Raymond C. Rowe (2009). Further, the skilled artisan will appreciate that certain excipients may be more desirable or suitable for certain modes of administration of an active ingredient. It is within the purview of the skilled artisan to select the appropriate excipients for a given pharmaceutical composition.

In one embodiment, a topical composition is provided which includes a topical excipient. For example, thickeners, diluents, emulsifiers, dispersing aids or binders may be used as needed. The topical excipient is selected so as to provide the composition in the desired form, e.g., as a liquid, lotion, cream, paste, gel, powder, or ointment, and may be comprised of a material of either naturally occurring or synthetic origin. Examples of suitable topical excipients for use herein include water, alcohols and other nontoxic organic solvents, glycerin, mineral oil, silicone, petroleum jelly, lanolin, fatty acids, vegetable oils, parabens, aloe vera, waxes, and the like.

Ointments and creams can, for example, be formulated with an aqueous or oily base with the addition of suitable thickening and/or gelling agents. Lotions can be formulated with an aqueous or oily base and will in general also containing one or more emulsifying agents, stabilizing agents, dispersing agents, suspending agents, thickening agents, or coloring agents.

In some embodiments, one function of the excipient is to enhance skin penetration of the active ingredients. Permeation enhancers are compounds which promote skin permeability by altering the skin as a barrier to the flux of a desired penetrant. These may be classified as solvents, surfactants and miscellaneous chemicals. Suitable excipients are well known to skilled practitioners, and include liposomes, ethanol, dimethylsulfoxide (DMSO), petroleum jelly (petrolatum), mineral oil (liquid petrolatum), water, dimethylformamide, dekaoxyethylene-oleylether, oleic acid, 2-pyrrolidone, Azone® brand penetration enhancer (Upjohn), biologically acceptable glycols, diglycols, polyglycols; alkyoxy C2-C8 alcohols, ethoxydiglycol and dimethyl isosorbide. A skin penetration enhancer may be included at concentrations ranging from about 5% to 95%, or more specifically from about 5% to 10% of the total composition.

In one embodiment, the concentration of Formula I or Formula II peptides in a pharmaceutical composition ranges from about 1 mg/ml to about 1000 mg/ml and includes all values and increments therebetween, especially including 1, 5, 10, 15, 20, 25, 30, 35, 40, 45, 50, 55, 60, 65, 70, 75, 80, 85, 90, 95, 100, 200, 300, 400, 500, 600, 700, 800, 900, and 1000 mg/ml. In another embodiment, the concentration of Formula I or Formula II peptides ranges from about 1 mg/ml to about 100 mg/ml, including all values and increments therebetween. In a specific embodiment, the concentration of Formula II or Formula II peptides ranges from about 1 mg/ml to about 50 mg/ml, including all values and increments therebetween. In a very specific embodiment, the concentration of Formula II or Formula II peptides is about 40 mg/ml.

In certain embodiments, the pharmaceutical composition is a topical composition comprising as a vehicle from about 20% to about 50% propylene glycol and from about 50% to about 80% water, with pH adjusted to 4.0 with 10 mM citric acid.

Pharmaceutical compositions disclosed herein are useful in the treatment of various skin disorders that benefit from agonism of MC1R. In one embodiment, skin disorders are selected from the group consisting of melanoma, basal cell carcinoma, squamous cell carcinoma, porphyria, polymorphous light eruption, vitiligo, and solar urticaria. In a specific embodiment, the skin disorder is melanoma.

Compositions described herein may further include a therapeutic amount of one or more additional active agents. For example, an additional active agent may be an antioxidant, a sunscreen, an anti-inflammatory agent, an anti-acne agent, a chemotherapeutic agent, or mixtures thereof.

In a specific embodiment, the second active agent is a chemotherapeutic agent selected from the group consisting of Aldesleukin (Proleukin®), Dabrafenib (Tafinlar®), Dacarbazine (Dtic-Dome®), Recombinant Interferon Alfa-2b (Intron A®), Ipilimumab (Yervoy®), Trametinib (Mekinist™), Peginterferon Alfa-2b (PegIntron®, Sylatron™), Trametinib, and Vemurafenib (Zelboraf®). In a very specific embodiment, the second active agent is Dacarbazine.

The peptide agonists of MC1R disclosed herein are highly selective for MC1R and are thus also useful in targeted delivery of agents to melanocytes. Thus, in one embodiment, the pharmaceutical compositions disclosed herein comprise peptide agonists conjugated to a second active agent desirably delivered to the melanocytes in the skin. Suitable conjugated second active agents include, but are not limited to, chemotherapeutic agents, including Dacarbazine, radioactive particles such as $^{212}$Pb, and radiometals, such as the metal chelator 1,4,7,10-tetrazocyclododecane 1,4,7,10-tetraacetic acid (DOTA), which can be labeled with $^{111}$In, for imaging of melanoma, mainly for detection of metastasis.

Methods of Use

The Formula I and Formula II MC1R peptide agonists and pharmaceutical compositions comprising the peptide agonists disclosed herein are useful in methods of treating skin disorders that benefit from agonism of MC1R.

In some embodiments, the methods for treating a skin disorder comprise administering to an individual in need thereof a therapeutic amount of a peptide agonist of MC1R as described herein. The peptide agonist, as set forth above, includes the agonist and its pharmaceutically acceptable salts, solvates, and enantiomers. In some embodiments, the peptide agonist is present in a pharmaceutical composition as described hereinabove.

The presently disclosed MC1R agonists provide therapy for a wide variety of skin disorders, including but not limited to, melanoma, basal cell carcinoma, squamous cell carcinoma, porphyria, polymorphous light eruption, vitiligo, and solar urticaria. In a specific embodiment, the skin disorder is associated with a loss-of-function allelic variant of MC1R gene. In another embodiment, the skin disorder is associated with a mutation of a predisposition gene, such as a gene selected from the group consisting of p16, p14 ARF, and CDK4.

A therapeutic amount, as defined herein in relation to the treatment of a skin disorder, is an amount which is sufficient to yield a desired therapeutic response without undue adverse side effects (such as toxicity, irritation, or allergic response) commensurate with a reasonable benefit/risk ratio when used in the manner of this disclosure. In some embodiments, a therapeutic amount of the peptide agonists described herein can be delivered topically to the skin of an individual. When administered topically, the peptide agonists disclosed herein are small in size and are lipophilic, thus able to effectively penetrate the upper layers of the skin and contact the melanocytes located in the basal layer of the epidermis.

In other embodiments, wherein such treatment is considered more suitable, a therapeutic amount of the peptide agonists disclosed herein can be administered systemically. For example, the peptide agonists can be administered via oral, intravenous, subcutaneous, intramuscular, intraperitoneal, sublingual, rectal, or nasal routes of delivery.

In one embodiment, the peptides and pharmaceutical compositions disclosed herein treat skin disorders by stimulating production of melanin by melanocytes, thereby providing increased skin protection from ultraviolet radiation. Surprisingly, it has been discovered that the MC1R agonists disclosed herein also directly activate DNA repair pathways, independently of the production of melanin, as repair of DNA damage can be measured prior to increase in melanin content of melanocytes. Further, these peptides prevent oxidative stress and oxidative DNA damage, thus inhibiting melanocyte death as in the case of vitiligo. Hence, the peptide agonists disclosed herein have wide application in treating and preventing skin disorders associated with DNA damage from UV light.

In addition, it will be appreciated that therapeutic benefits for the treatment of certain skin disorders can be realized by combining treatment with one or more additional active agents. The choice of such combinations will depend on various factors including, but not limited to, the type of skin disorder, the age and general health of the individual, the aggressiveness of disease progression, and the ability of the individual to tolerate the agents that comprise the combination.

In certain embodiments, the additional active agent comprises an antioxidant, a sunscreen, an anti-inflammatory agent, an anti-acne agent, a chemotherapeutic agent, or combinations thereof.

In a specific embodiment, the additional active agent comprises a sunscreen selected from the group consisting of titanium dioxide, zinc oxide, PABA esters (glyceryl, padimate A and padimate O), salicylates (homosalate, octyl salicylate), cinnamates (cinoxate, octyl methoxycinnamate, octocrylene), benzophenones, ecamsule (Mexoryl™), and the like.

In another embodiment, the second agent comprises a chemotherapeutic agent selected from the group consisting of Aldesleukin (Proleukin®), Dabrafenib (Tafinlar®), Dacarbazine (Dtic-Dome®), Recombinant Interferon Alfa-2b (Intron A®), Ipilimumab (Yervoy®), Trametinib (Mekinist™), Peginterferon Alfa-2b (PegIntron®, Sylatron™), Trametinib, and Vemurafenib (Zelboraf®). In a very specific embodiment, the second active agent is Dacarbazine.

Combination treatments involving the peptides disclosed herein and another active agent can be achieved by administering both agents at substantially the same time. Alternatively, treatment with the peptide agonists disclosed herein can precede or follow treatment with the other agent by intervals ranging from minutes to weeks.

In another embodiment, the peptide agonists of MC1R disclosed herein are highly selective for MC1R and are thus also useful in targeted delivery of agents to melanocytes. Thus, in one embodiment, Formula I and Formula II peptides may be conjugated to a second active ingredient, in order to facilitate delivery of the second active agent to the melanocytes. A method of delivering a second active agent to a melanocyte is provided, the method comprising administering a therapeutic amount of a Formula I or Formula II peptide conjugated to the second active agent, or a pharmaceutical composition comprising the same. Suitable conjugated second active agents include, but are not limited to, chemotherapeutic agents, including Dacarbazine, radioactive particles such as $^{212}$Pb, and radiometals, such as the metal chelator 1,4,7,10-tetrazocyclododecane 1,4,7,10-tetraacetic acid (DOTA), which can be labeled with $^{111}$In, for imaging of melanoma, mainly for detection of metastasis.

Accordingly, in one embodiment, a pharmaceutical composition is provided, the pharmaceutical composition comprising:

(a) an effective amount of a selective peptide agonist of melanocortin 1 receptor (MC1R) according to the formula:

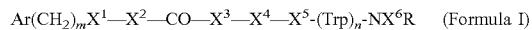

$$Ar(CH_2)_m X^1 - X^2 - CO - X^3 - X^4 - X^5 - (Trp)_n - NX^6 R \quad \text{(Formula I)}$$

or a pharmaceutically acceptable salt, solvate, or enantiomer thereof, wherein:

Ar is selected from the group consisting of unsubstituted or substituted phenyl and 5- or 6-membered heteroaryl;

m is 0, 1, 2, or 3;

$X^1$ is absent or $X^1$ is selected from the group consisting of O, NR', S, Se, and CR'R" wherein R' is selected from the group consisting of H, linear or branched C1-C4 alkyl, OH, and linear or branched C1-C4O-alkyl and R" is selected from the group consisting of H and linear or branched C1-C4 alkyl; or wherein CR'R" is a C3-C6 cycloalkyl;

$X^2$ is absent or $X^2$ is selected from the group consisting of 1,2-phenylene, 1,3-phenylene, 1,4-phenylene, and CQ'Q" wherein Q' and Q" are each independently selected from the group consisting of H and linear or branched C1-C4 alkyl;

$X^3$ is selected from the group consisting of unsubstituted or substituted L-histidine (His), 3-(2-pyridyl)-L-alanine (2-PAL), 3-(3-pyridyl )-L-alanine (3-PAL), 3-(4-pyridyl)-L-alanine (4-PAL), 3-(2-thienyl)-L-alanine (2-Thi), 3-(3-thienyl)-L-alanine (3-Thi), 3-(2-furyl)-L-alanine (2-FurAla), 3-(3-furyl)-L-alanine (2-FurAla), L-homoserine (HoSer), O-methyl-L-homoserine (HoSer(Me)), and L-allylglycine;

$X^4$ is selected from the group consisting of unsubstituted or substituted D-phenylalanine (D-Phe), L-alpha-MePhe, 3-(2-thienyl)-D-alanine (D-2-Thi), 3-(3-thienyl)-D-alanine (D-3-Thi), 3-(2-furyl)-D-alanine (D-2-FurAla), and 3-(3-furyl)-D-alanine (D-3-FurAla);

$X^5$ is selected from the group consisting of unsubstituted or substituted L-arginine (Arg) and L-citrulline;

n is 0 or 1;

$X^6$ is selected from the group consisting of H, linear or branched C1-C4 alkyl, and C3-C4 cycloalkyl; and R is selected from the group consisting of H, linear or branched C1-C12 alkyl, linear or branched C1-C12 arylalkyl, and C3-C5 cycloalkyl;

or wherein $X^6$ and R together form a C3-C5 cycloalkyl; and (b) one or more pharmaceutically acceptable excipients.

In one embodiment, substituted D-Phe comprises D-4-t-Bu-phenylalanine (D-4-tBuPhe), D-alpha-methylphenylalanine (D-alpha-MePhe), D-4-biphenylalanine (D-4-Bip), D-1-naphthylalanine (D-1-Nal), D-2-naphthylalanine (D-2-Nal), 4-FPhe, 4-ClPhe, 4-BrPhe, 4-IPhe, 4-NO$_2$Phe, or 3-NO$_2$Phe.

In another embodiment, Ar is selected from the group consisting of unsubstituted or substituted phenyl and 5- or 6-membered heteroaryl; m is 1, 2, or 3; $X^1$ is absent; $X^2$ is absent; $X^3$ is His; $X^4$ is selected from the group consisting of D-Phe, D-2-Thi, D-3-Thi, D-4-tBuPhe, D-alpha-MePhe, L-alpha-MePhe, D-4-Bip, D-1-Nal, and D-2-Nal; $X^5$ is selected from the group consisting of unsubstituted or substituted Arg and L-citrulline; n is 0 or 1; $X^6$ is selected from the group consisting of H, linear or branched C1-C4 alkyl, and C3-C4 cycloalkyl; and R is selected from the group consisting of H, linear or branched C1-C12 alkyl, linear or branched C1-C12 arylalkyl, and C3-05 cycloalkyl.

In a specific embodiment, Ar is unsubstituted or substituted phenyl; m is 3; $X^1$ is absent; $X^2$ is absent; $X^3$ is His; $X^4$ is selected from the group consisting of D-4-tBuPhe, D-4-Bip, D-1-Nal, and D-2-Nal; $X^5$ is unsubstituted or substituted Arg; n is 0 or 1; $X^6$ is H, methyl, or ethyl; and R is H, methyl, or ethyl.

In another embodiment, $X^4$ is in the D stereoisomer configuration.

In still another embodiment, Ar is unsubstituted or substituted phenyl. In another embodiment, m is 3 and $X^1$ and $X^2$ are absent. In another embodiment, $X^3$ is His. In another embodiment, $X^4$ is selected from the group consisting of D-Phe, D-4-tBuPhe, D-4-Bip, D-1-Nal, and D-2-Nal. In another embodiment, $X^5$ is Arg. In still another embodiment, $X^6$ is H and R is H, methyl, or ethyl.

In a specific embodiment, the agonist is selected from the group consisting of Ph(CH$_2$)$_3$CO-His-(D-Phe)-Arg-Trp-NHEt; Ph(CH$_2$)$_3$CO-His-(D-1-Nal)-Arg-Trp-NH$_2$; Ph(CH$_2$)$_3$CO-His-(D-4-Bip)-Arg-NH$_2$; Ph(CH$_2$)$_3$CO-His-(D-4-Bip)-Arg-NHMe; and Ph(CH$_2$)$_3$CO-His-(D-4-tBuPhe)-Arg-NH$_2$.

In another embodiment, a pharmaceutical composition is provided wherein the selective peptide agonist of MC1R is substantially free from conformational restraints imposed by secondary structure. In a specific embodiment, the selective peptide agonist of MC1R is not constrained by a beta-turn conformation.

Also provided herein is a method of treating a skin disorder, the method comprising administering to an individual in need thereof a therapeutic amount of a pharmaceutical composition comprising a Formula I or Formula II peptide agonist. In one embodiment, the skin disorder is selected from the group consisting of melanoma, basal cell carcinoma, squamous cell carcinoma, porphyria, polymorphous light eruption, vitiligo, and solar urticaria. In another embodiment, the skin disorder is associated with a loss-of-function allelic variant of melanocortin 1 receptor (MC1R) gene. In another embodiment, the skin disorder is associated with a mutation of a predisposition gene. In a specific embodiment, the predisposition gene is selected from the group consisting of p16, p14 ARF, and CDK4. In another embodiment, the skin disorder is a disorder that benefits from agonism of melanocortin 1 receptor (MC1R).

In a specific embodiment, the methods provided herein deliver the selective peptide agonist of MC1R to melanocytes in the skin. In one aspect, the selective peptide agonist of MC1R stimulates production of melanin by melanocytes, thereby providing increased skin protection from ultraviolet radiation. In another aspect, the selective peptide agonist of MC1R activates DNA repair pathways. In another embodiment, the selective peptide agonist of MC1R inhibits oxidative stress that can cause melanocyte death, as in the case of vitiligo.

In one embodiment, administering comprises topical or systemic administration.

In another embodiment, the methods disclosed herein further comprise administering a sunscreen.

In still another embodiment, pharmaceutical compositions and methods of use comprise a selective peptide MC1R agonist according to Formula I or Formula II, wherein the agonist is conjugated to a second active agent. In one aspect, the selective peptide agonist of MC1R targets delivery of the second active agent. In a specific aspect, the selective peptide agonist of MC1R delivers the second pharmaceutical agent to melanocytes in the skin.

EXAMPLES

The following examples are given by way of illustration and are in no way intended to limit the scope of the present invention.

Example 1

Selectivity of Peptide Agonists for Human Melanocortin 1 Receptor (hMC1R)

Receptor selectivity of peptide agonists for hMC1R was determined by stimulation of cAMP in heterologous cells expressing different human melanocortin receptors (MC1R, MC3R, MC4R, and MC5R). Tested peptides included the following: melanotan II (MT-II), alpha melanocortin stimulating hormone (α-MSH), LK-184 (Ph(CH$_2$)$_3$CO-His-(D-Phe)-Arg-Trp-NH$_2$), LK-467 (Ph(CH$_2$)$_3$CO-His-(D-1-Nal)-Arg-Trp-NH$_2$), LK-511 (Ph(CH$_2$)$_3$CO-His-(D-4-Bip)-Arg-NH$_2$), LK-513 (Ph(CH$_2$)$_3$CO-His-(D-4-Bip)-Arg-NHMe) and LK-514 (Ph(CH$_2$)$_3$CO-His-(D-4-tBuPhe)-Arg-NH$_2$). Results are shown in Table 1 below:

TABLE 1

| | Melanocortin Receptor Selectivity | | | | | | | |
|---|---|---|---|---|---|---|---|---|
| | HMC1R | | HMC3R | | HMC4R | | HMC5R | |
| | EC50 (NM) | % MAX. ACTIVITY | EC50 (NM) | % MAX. ACTIVITY | EC50 (NM) | % MAX. ACTIVITY | EC50 (NM) | % MAX. ACTIVITY |
| MT-II | 3.57 | 103 | — | — | — | — | 51.66 | 100 |
| α-MSH | — | — | 6.11 | 100 | 16.0 | 100 | — | — |
| LK-184 | 0.19 | 128 | 22.7 | 85 | 1.69 | 102 | 262.3 | 39 |
| LK-467 | 0.34 | 111 | 32.4 | 7 | 18.1 | 39 | 122.0 | 34 |
| LK-511 | 1.46 | 88 | | | INACTIVE | | | |
| LK-513 | 3.27 | 95 | | | EC$_{50}$>10000 (2-7% MAX. ACTIVITY) | | | |
| LK-514 | 3.65 | 94 | | | | | | |

Results show that LK-467 is about ten times less potent in binding the undesirable hMC4R than tetrapeptide LK-184. Tripeptides LK-511, LK-513, and LK-514 are about as potent as MT-II with respect to activation of MC1R, but are selective for activating MC1R and do not bind MC3R, MC4R, or MC5R. Results indicate that simultaneous introduction of hydrophobic substituents at the D-Phe position and the N- and/or C-terminus of LK-184 results in more potent, selective MC1R peptide agonists.

Example 2

Peptide Stability

LK-513 (Ph(CH$_2$)$_3$CO-His-(D-4-Bip)-Arg-NHMe) was tested for stability and degradation over a storage period. The peptide was stored in a lyophilized form in open air at room temperature for 4 months. After 4 months, HPLC was performed on a test sample of the peptide in order to measure degradation, using standard methods (FIG. 1). The peptide is highly stable and resistant to degradation, showing only a single HPLC peak. Without being bound by theory, it is believed that the enhanced stability is a product of the absence of amide bonds between natural L-L-amino acids in the tripeptides and the existence of only one amide bond between natural amino acids in the tetrapeptides (Arg-Trp). Amide bonds between non-natural D- and natural L-amino acids are less prone to chemical and enzymatic hydrolysis, as evidenced by the FIG. 1. Further, the bulk and hydrophobicity of the X4 amino acid (D-Phe or a bulky hydrophobic analog thereof, such as D-4-Bip in the case of LK-513) shield the polar amid bonds of the peptide from chemical and enzymatic degradation.

Example 3

Dose-Dependent Stimulation of cAMP in Human Melanocytes

Figure 2:
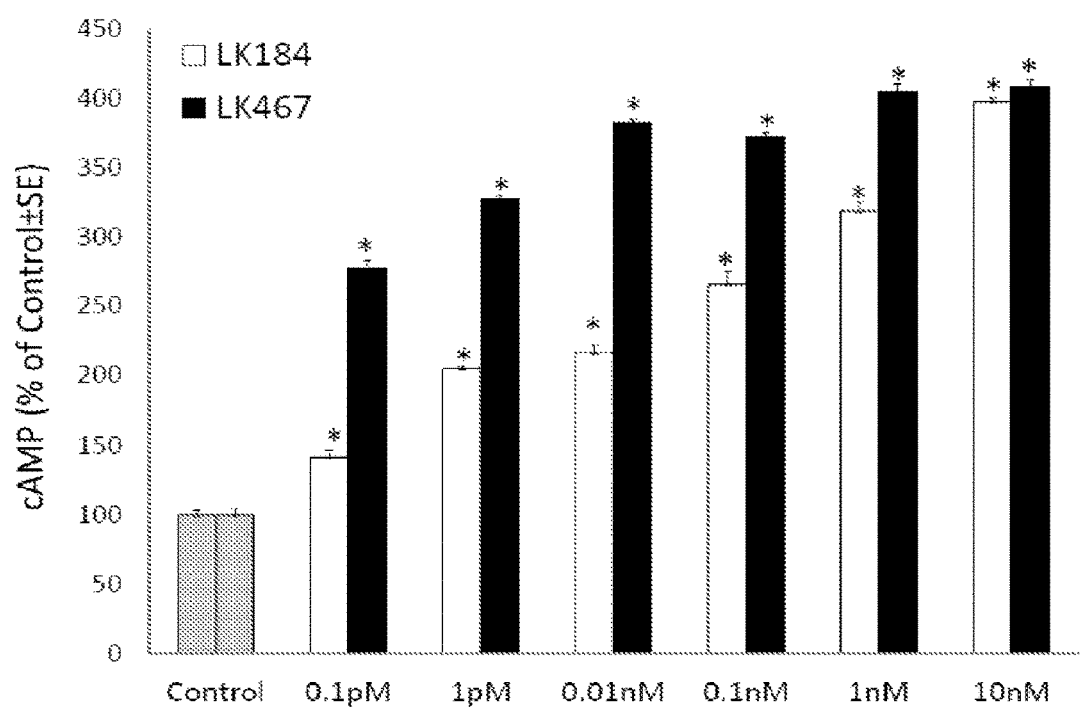
FIG. 2 shows dose-dependent stimulation of cAMP in human melanocytes by tetrapeptides LK-184 and LK-467. Results indicate maximal cAMP for LK-467 was achieved at 0.01 nM, compared to 10 nM for LK-1 84, a lead tetrapeptide.
Figure 3:
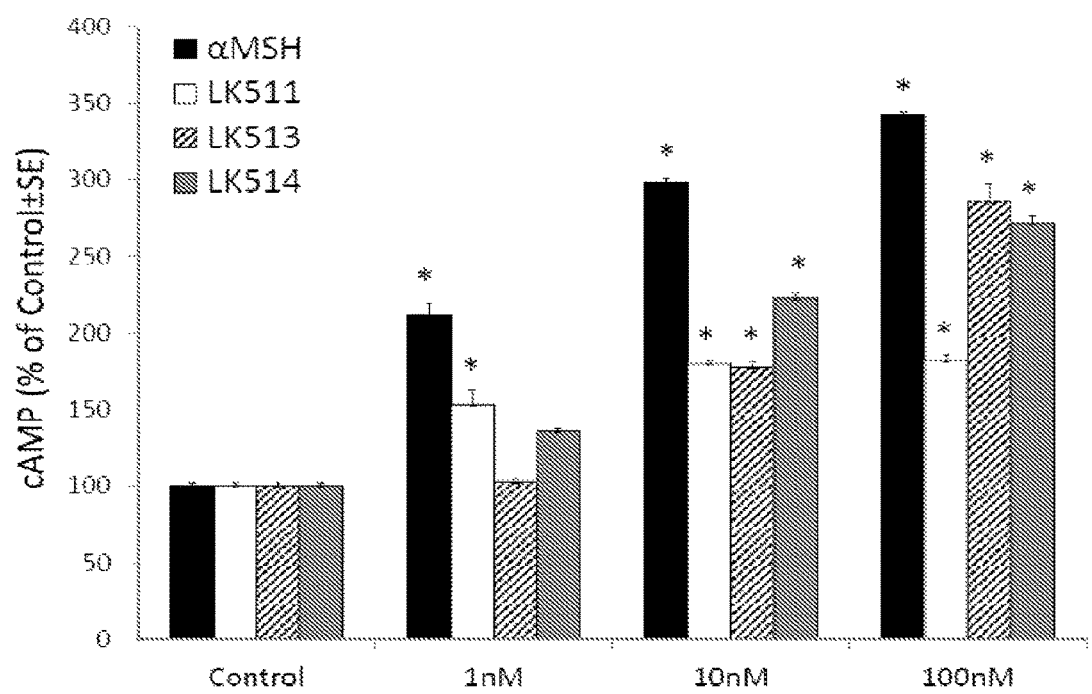
FIG. 3 shows dose-dependent stimulation of cAMP in human melanocytes by the tripeptides LK-511, LK-513, and LK-514, in comparison to alpha-MSH (α-MSH). Results indicate the tripeptides LK-511, LK-513, and LK-514 were about ten times less potent than α-MSH in increasing cAMP formation, with LK-514 being more potent than LK-511 or LK-513

Peptides were tested on cultured human melanocytes for their capacity to activate MC1R, as measured by stimulating cAMP formation. After 45 minutes of treatment with different concentrations of peptides, cAMP levels were measured using a I$^{125}$-labeled radioimmunoassay kit. Tetrapeptide LK-467 proved to be more potent than LK-184 in stimulating cAMP formation, resulting in maximal levels of cAMP at a concentration of 0.1 nM, compared to 10 nM of LK-184 (FIG. 2). Tetrapeptide LK-487 was equipotent to LK-467 in this assay (data not shown). The tripeptides LK-511, LK-513, and LK-514 were about ten times less potent than a-MSH in increasing cAMP formation, with LK-514 being more potent than LK-511 or 513 (FIG. 3). These results demonstrate that these small peptides have remarkable potency to activate the MC1R.

Example 4

Dose-Dependent Stimulation of Tyrosinase Activity

Figure 4:
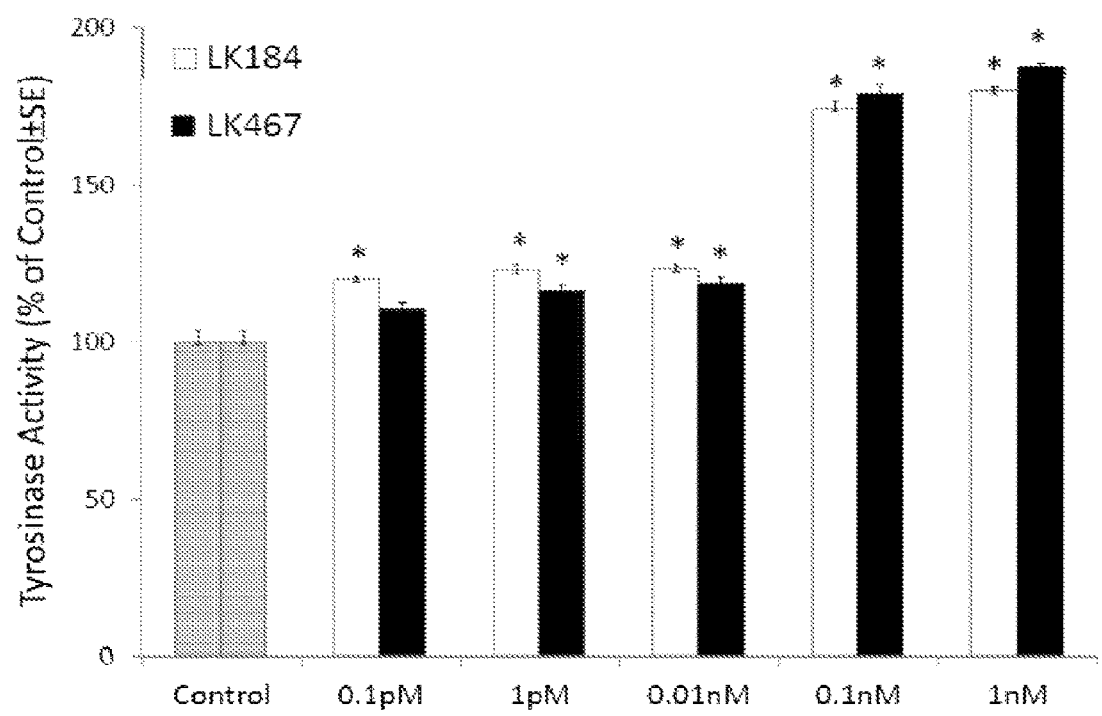
FIG. 4 shows dose-dependent stimulation of the activity of tyrosinase, the rate limiting enzyme for melanin synthesis, by LK-184 and LK-467. Results indicate that tetrapeptides LK-467 and LK-184 had comparable effects in tyrosinase activity.
Figure 5:
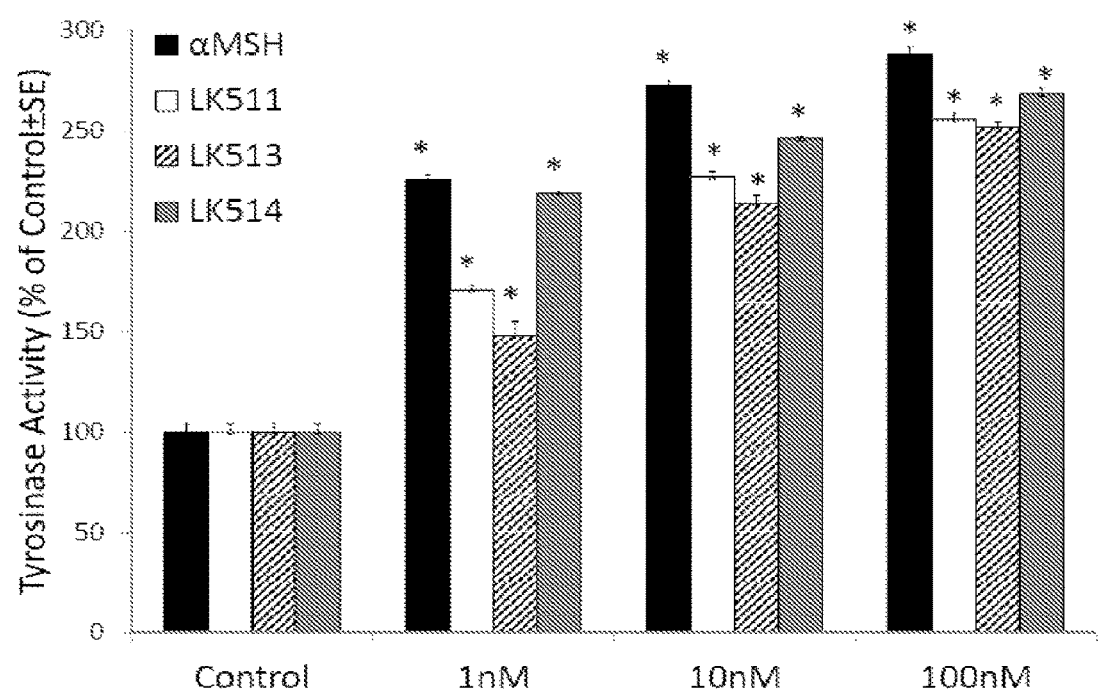
FIG. 5 shows dose-dependent stimulation of tyrosinase activity by LK-511, LK-513, and LK-514, in comparison to α-MSH. Results indicate that tripeptides LK-511, LK-513, and LK-514 resulted in significant stimulation of tyrosinase activity beginning at 1 nM.

Peptides were tested on cultured human melanocytes for their capacity for stimulating tyrosinase activity, the rate-limiting enzyme for melanin synthesis. Melanocytes were treated every other day, for a total of 6 days, with increasing concentrations of peptides. Medium containing H$^3$-tyrosine, the substrate for tyrosinase, was added to melanocytes 24 hours before the end of the 6-day treatment. Tyrosinase activity was measured by determining the amount of $^3$H$_2$O generated as H$^3$-tyrosinase is catalyzed by tyrosinase for melanin synthesis. Tetrapeptides LK-467 and LK-184 had comparable effects in tyrosinase activity, indicating that LK-467 is at least 100 times more potent than a-MSH in activating MC1R and stimulating melanogenesis (FIG. 4). Tetrapeptide LK-487 was equipotent to LK-467 in this assay (data not shown). The tripeptides LK-511, LK-513, and LK-514 resulted in significant stimulation of tyrosinase activity beginning at 1 nM, with LK-514 being the most effective (FIG. 5). These results demonstrate that these small peptides have remarkable potency to activate MC1R and stimulate melanogenesis.

Example 5

Repair of UV-induced Cyclobutane Pyrimidine Dimers

Figure 6:
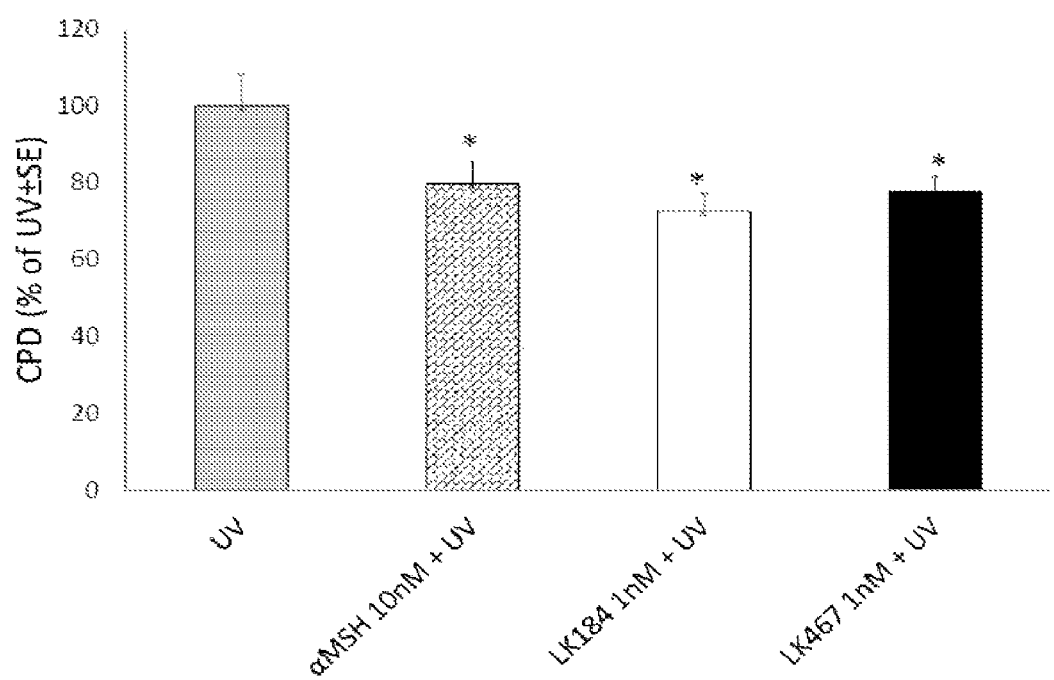
FIG. 6 shows repair of UV-induced DNA damage via reduction of the levels of cyclobutane pyrimidine dimers (CPD), the major form of DNA photoproducts, 48 hours post UV exposure of human melanocytes, with or without peptide treatment. Results show that LK-467 was as effective as LK-184 in reducing CPD levels 48 hours after exposure. Both peptides had the same effect at 1 nM on CPD removal as 10 nM α-MSH.
Figure 7:
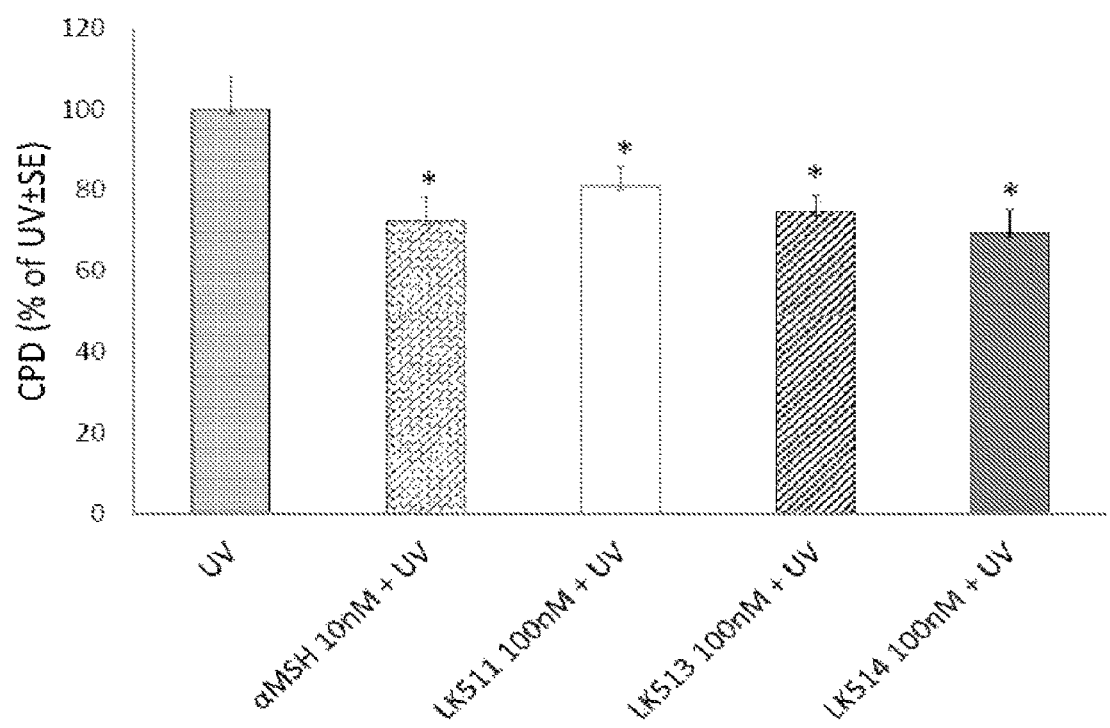
FIG. 7 shows repair of UV-induced DNA damage via reduction of the levels of CPD 48 hours post UV exposure of human melanocytes, with or without peptide treatment. The tripeptides LK-511, LK-513, and LK-514 had similar effect at 100 nM compared to 10 nM α-MSH.

To investigate the effects of peptides on the repair of UV-induced DNA damage, levels of cyclobutane pyrimidine dimers (CPD), the major form of DNA photoproducts, were measured in UV-irradiated human melanocytes with or without peptide treatment. Melanocytes were pretreated with the peptides for 4 days prior to, and for 48 hours post UV exposure, harvested, immunostained by a specific antibody for CPD, and analyzed by flow cytometry. Results show that LK-467 was as effective as LK-184 in reducing CPD levels 48 hours after exposure. Both peptides had the same effect at 1 nM on CPD removal as 10 nM a-MSH (FIG. 6). The tripeptides LK-511, LK-513, and LK-514 at 100 nM had similar effect (FIG. 7). These results demonstrate that these small peptides have profound effects on reducing levels of UV-induced DNA damage, thus reducing the chance of mutations and malignant transformation of melanocytes to melanoma, a mechanism expected to prevent melanoma formation.

Example 6

Repair of UV-induced 8-oxodeoxyguanosine (8-oxodG)

Figure 8:
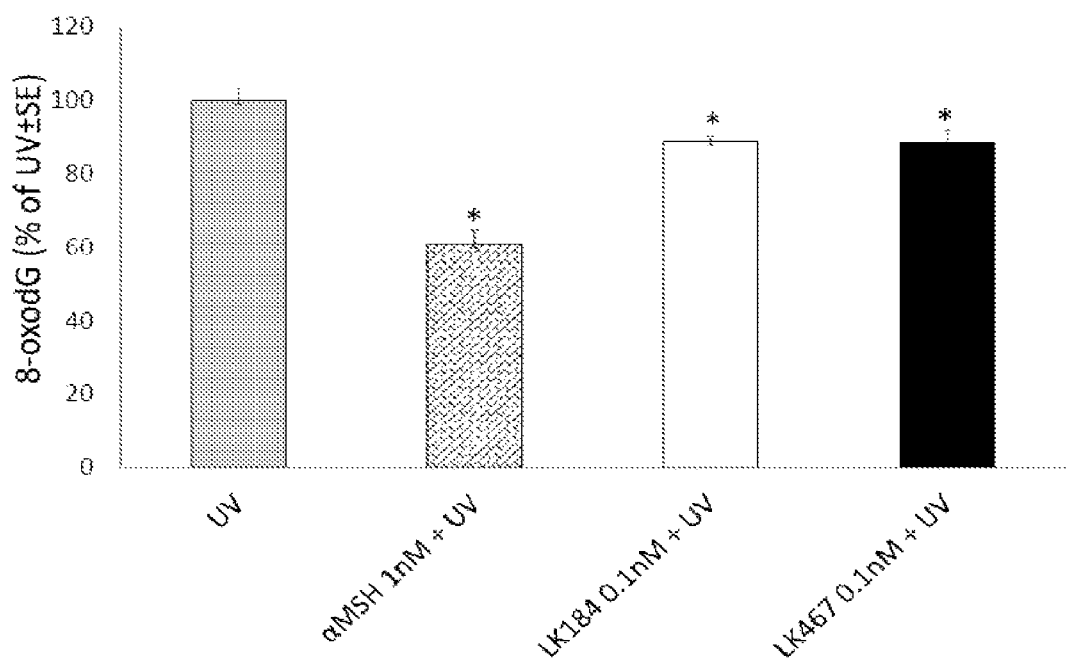
FIG. 8 shows repair of UV-induced oxidative DNA damage via reduction of the levels of 8-oxodG, the major form of damage, measured in human melanocytes 24 hours post UV exposure, with or without peptide treatment. Results show that LK-467 was as effective as LK-184 in reducing 8-oxodG levels 24 hours after UV exposure.
Figure 9:
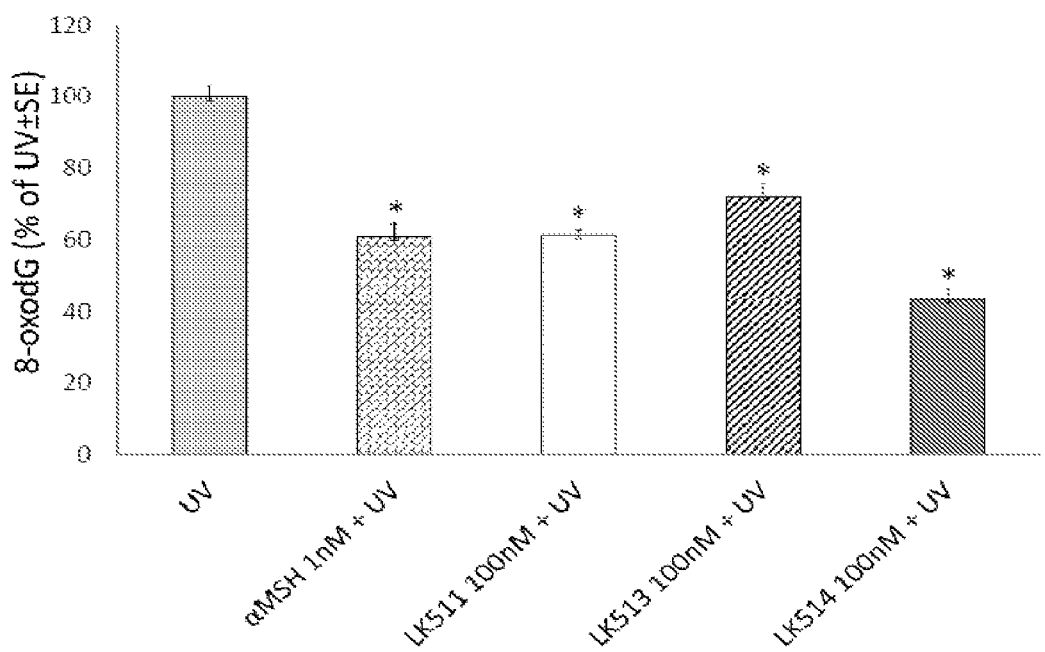
FIG. 9 shows repair of oxidative UV-induced DNA damage via reduction of the levels of 8-oxodG measured in human melanocytes 24 hours post UV exposure, with or without peptide treatment. When tested at 100 nM, tripeptides LK-511 and LK-513 had similar effect, while LK-514 had greater effect than 1 nM α-MSH in reducing the levels of 8-oxodG.

To investigate the effects of peptides on repair of UV-induced DNA damage, levels of 8-oxodG, a major form of oxidative DNA damage, were measured in UV-irradiated human melanocytes with or without peptide treatment. Melanocytes were pretreated with the respective peptide for 4 days prior, and 24 days post UV exposure and immunostained with 8-oxodG-specific antibody. Fluorescence intensity, which correlates with the amount of DNA damage, was quantified using ImagJ software. Results show that LK-467 was as effective as LK-184 in reducing 8-oxodG levels 24 hours after exposure (FIG. 8). When tested at 100 nM, tripeptides LK-511 and LK-513 had similar effect, while LK-514 had greater effect than 1 nM α-MSH in reducing the levels of 8-oxodG (FIG. 9). These results demonstrate that these small peptides have profound effects on reducing levels of UV-induced oxidative DNA damage, thus reducing the chance of mutations that lead to melanoma, and enhancing the survival of melanocytes to maintain photoprotection, and prevent depigmentation, the hallmark of vitiligo.

Example 7 cAMP and Tyrosinase Activity

Peptides were tested as described in Example 4 above on cultured human melanocytes for their capacity to activate MC1R, as measured by stimulating cAMP formation, and for their capacity for stimulating tyrosinase activity, the rate-limiting enzyme for melanin synthesis. The tested peptides were synthesized according to the formula:

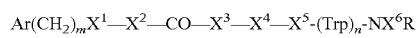

$$Ar(CH_2)_m-X^1-X^2-CO-X^3-X^4-X^5-(Trp)_n-NX^6R$$

wherein $X^1$ and $X^2$ are absent, $X^3$ is His, $X^5$ is Arg, and $X^6$ is H. $X^4$ amino acids were in the D-stereoisomer form, unless otherwise noted. Results are shown in Table 2, below.

TABLE 2 cAMP and Tyrosinase Activity Compared to 10 nM a-MSH

| LK | Ar | m | $X^4$ | n | R | cAMP compared to 10 nM αMSH | TA compared to 10 nM αMSH |
|---|---|---|---|---|---|---|---|
| 480P | 4-FC6H4 | 1 | Phe | 1 | H | << | < |
| 205P | 4-FC6H4 | 1 | 4-FPhe | 1 | H | ≤ | ≥ |
| 252P | 4-FC6H4 | 1 | 4-FPhe | 1 | Et | NR | |
| 206P | 4-HOC6H4 | 1 | 4-FPhe | 1 | H | < | |
| 208P | 4-BrC6H4 | 1 | 4-FPhe | 1 | H | > | |
| 210P | 3,4-CH2O2 | 1 | 4-FPhe | 1 | H | ≥ | |
| 470P | Ph | 3 | 4-FPhe | 1 | H | > | |
| 473P | Ph | 3 | 4-ClPhe | 1 | H | =; > | |
| 474P | Ph | 3 | 4-BrPhe | 1 | H | =; <; > | |
| 475P | Ph | 3 | 4-Iphe | 1 | H | <; > | |
| 476P | Ph | 3 | 2-Thi | 1 | H | > | |
| 467P | Ph | 3 | 1-Nal | 1 | H | > | |
| 468P | Ph | 3 | 2-Nal | 1 | H | ≤ | |
| 471P | Ph | 3 | 4-NO2Phe | 1 | H | = | |
| 472P | Ph | 3 | 3-NO2Phe | 1 | H | < | |
| 469P | Ph | 3 | 4-Bip | 1 | H | ≤; > | |
| 480P | 4-FPh | 1 | Phe | 1 | H | < | |
| 486P | Ph | 3 | Phe | 0 | Et | << | |
| 487P | Ph | 3 | Phe | 1 | Et | >* | |
| 488P | 4-IPH | 1 | Phe | 1 | H | >> | |
| 489P | 4-IPH | 1 | 4-IPhe | 0 | H | ≤ | |
| 491P | Ph | 3 | 1-Nal | 0 | Et | NR | |
| 492P | Ph | 3 | 2-Nal | 0 | Et | NR | |
| 493P | Ph | 3 | 4-Bip | 0 | Et | << | |
| 494P | Ph | 3 | 4-tBuPhe | 0 | Et | << | |
| 495P | 4-FPh | 1 | 1-Nal | 0 | Et | NR | |
| 496P | 4-FPh | 1 | 2-Nal | 0 | Et | NR | |
| 497P | 4-FPh | 1 | 4-Bip | 0 | Et | NR | |
| 498P | 4-FPh | 1 | 4-tBuPhe | 0 | Et | NR** | |
| 503P | 4-FPh | 1 | α-MePhe | 0 | Et | < | |
| 510P | Ph | 3 | 1-Nal | 0 | H | | NR |
| 511P | Ph | 3 | 4-Bip | 0 | H | < | < |
| 512P | Ph | 3 | 1-Nal | 0 | Me | | NR |
| 513P | Ph | 3 | 4-Bip | 0 | Me | < | < |
| 514P | Ph | 3 | 4-tBuPhe | 0 | H | < | < |
| 515P | Ph | 3 | 2-Nal | 0 | H | | << |
| 516P | Ph | 3 | 4-tBuPhe | 0 | Me | | << |
| 517P | Ph | 3 | 2-Nal | 0 | Me | | <<< |

NR = No Response/inactive at 10 nM
*better responder than α-MSH
**potential antagonist Example 8

Tri- and Tetrapeptides

Examples of Formula I peptides are shown in Table 2, below.

TABLE 2

Formula I Peptides
$Ar(CH_2)_m X^1\text{-}X^2\text{-}CO\text{-}X^3\text{-}X^4\text{-}X^5\text{-}(Trp)_n\text{-}NX^6R$ Ph(CH$_2$)$_3$CO-His-(D-Phe)-Arg-Trp-NHEt
Ph(CH$_2$)$_3$CO-His-(D-1-Nal)-Arg-Trp-NHEt
Ph(CH$_2$)$_3$CO-His-(D-2-Nal)-Arg-Trp-NHEt
Ph(CH$_2$)$_3$CO-His-(D-4-Bip)-Arg-Trp-NHEt
Ph(CH$_2$)$_3$CO-His-(D-4-tBuPhe)-Arg-Trp-NHEt
4-FC$_6$H$_4$CH$_2$CO-His-(D-Phe)-Arg-Trp-NHEt
4-FC$_6$H$_4$CH$_2$CO-His-(D-1-Nal)-Arg-Trp-NHEt
4-FC$_6$H$_4$CH$_2$CO-His-(D-2-Nal)-Arg-Trp-NHEt
4-FC$_6$H$_4$CH$_2$CO-His-(D-4-Bip)-Arg-Trp-NHEt
4-FC$_6$H$_4$CH$_2$CO-His-(D-4-tBuPhe)-Arg-Trp-NHEt TABLE 2-continued Formula I Peptides
$Ar(CH_2)_m X^1\text{-}X^2\text{-}CO\text{-}X^3\text{-}X^4\text{-}X^5\text{-}(Trp)_n\text{-}NX^6R$ Ph(CH$_2$)$_3$CO-His-(D-Phe)-Arg-Trp-NHMe
4-FC$_6$H$_4$CH$_2$CO-His-(D-Phe)-Arg-Trp-NHMe
Ph(CH$_2$)$_3$CO-His-(D-1-Nal)-Arg-Trp-NH$_2$
Ph(CH$_2$)$_3$CO-His-(D-2-Nal)-Arg-Trp-NH$_2$
4-BrC$_6$H$_4$CH$_2$CO-His-(D-Phe)-Arg-Trp-NH$_2$
4-FC$_6$H$_4$CH$_2$CO-His-(D-4-FPhe)-Arg-Trp-NH$_2$
4-BrC$_6$H$_4$CH$_2$CO-His-(D-4-FPhe)-Arg-Trp-NH$_2$
4-CF3C$_6$H$_4$CH$_2$CO-His-(D-4-FPhe)-Arg-Trp-NH$_2$
3,4-O(CH$_2$)$_2$C$_6$H$_4$CH$_2$CO-His-(D-4-FPhe)-Arg-Trp-NH$_2$
(D)-C$_6$H$_5$C$_6$H$_4$CH(OH)CO-His-(D-4-FPhe)-Arg-Trp-NH$_2$
(L)-C$_6$H$_5$C$_6$H$_4$CH(OH)CO-His-(D-4-FPhe)-Arg-Trp-NH$_2$
(D,L)-C$_6$H$_5$C$_6$H$_4$CH(OH)CO-His-(D-4-FPhe)-Arg-Trp-NH$_2$
(D,L)-C$_6$H$_5$C$_6$H$_4$CH(OMe)CO-His-(D-4-FPhe)-Arg-Trp-NH$_2$
(D)-4-ClC$_6$H$_4$CH(OH)CO-His-(D-4-FPhe)-Arg-Trp-NH$_2$
(L)-4-ClC$_6$H$_4$CH(OH)CO-His-(D-4-FPhe)-Arg-Trp-NH$_2$
(D,L)-4-ClC$_6$H$_4$CH(OH)CO-His-(D-4-FPhe)-Arg-Trp-NH$_2$
C$_6$F$_5$CH$_2$CO-His-(D-4-FPhe)-Arg-Trp-NH$_2$
4-C$_6$H$_5$C$_6$H$_4$CO-His-(D-4-FPhe)-Arg-Trp-NH$_2$
4-C$_6$H$_5$OC$_6$H$_4$CO-His-(D-4-FPhe)-Arg-Trp-NH$_2$
3-C$_6$H$_5$OC$_6$H$_4$CO-His-(D-4-FPhe)-Arg-Trp-NH$_2$
Ph(CH$_2$)$_3$CO-His-(D-4-FPhe)-Arg-Trp-NH$_2$
Ph(CH$_2$)$_3$CO-His-(D-4-ClPhe)-Arg-Trp-NH$_2$
Ph(CH$_2$)$_3$CO-His-(D-4-BrPhe)-Arg-Trp-NH$_2$
Ph(CH$_2$)$_3$CO-His-(D-4-IPhe)-Arg-Trp-NH$_2$
Ph(CH$_2$)$_3$CO-His-(D-2-Thi)-Arg-Trp-NH$_2$
Ph(CH$_2$)$_3$CO-His-(D-4-NO$_2$Phe)-Arg-Trp-NH$_2$
Ph(CH$_2$)$_3$CO-His-(D-3-NO$_2$Phe)-Arg-Trp-NH$_2$
4-IC$_6$H$_4$CH$_2$CO-His-(D-Phe)-Arg-Trp-NH$_2$
4-IC$_6$H$_4$CH$_2$CO-His-(D-4-IPhe)-Arg-Trp-NH$_2$
Ph(CH$_2$)$_3$CO-His-(D-Phe)-Arg-Trp-NH$_2$
Ph(CH$_2$)$_3$CO-(4-PAL)-(D-Phe)-Arg-Trp-NH$_2$
Ph(CH$_2$)$_3$CO-(2-Thi)-(D-Phe)-Arg-Trp-NH$_2$
Ph(CH$_2$)$_3$CO-(3-Thi)-(D-Phe)-Arg-Trp-NH$_2$
Ph(CH$_2$)$_3$CO-(2-FurAla)-(D-Phe)-Arg-Trp-NH$_2$
Ph(CH$_2$)$_3$CO-(HoSer)-(D-Phe)-Arg-Trp-NH$_2$
Ph(CH$_2$)$_3$CO-(HoSer(Me))-(D-Phe)-Arg-Trp-NH$_2$
Ph(CH$_2$)$_3$CO-(AllGly)-(D-Phe)-Arg-Trp-NH$_2$
Ph(CH$_2$)$_3$CO-His-(D-1-Nal)-Arg-NH$_2$
Ph(CH$_2$)$_3$CO-His-(D-2-Nal)-Arg-NH$_2$
Ph(CH$_2$)$_3$CO-His-(D-4-Bip)-Arg-NH$_2$
Ph(CH$_2$)$_3$CO-His-(D-4-tBuPhe)-Arg-NH$_2$
4-BrC$_6$H$_4$CH$_2$CO-His-(D-4-FPhe)-Arg-NH$_2$
4-HOC$_6$H$_4$CH$_2$CO-His-(D-4-FPhe)-Arg-NH$_2$
3,4-O(CH$_2$)$_2$C$_6$H$_4$CH$_2$CO-His-(D-4-FPhe)-Arg-NH$_2$
Ph(CH$_2$)$_3$CO-His-(D-1-Nal)-Arg-NHMe
Ph(CH$_2$)$_3$CO-His-(D-2-Nal)-Arg-NHMe
Ph(CH$_2$)$_3$CO-His-(D-4-Bip)-Arg-NHMe
Ph(CH$_2$)$_3$CO-His-(D-4-tBuPhe)-Arg-NHMe
Ph(CH$_2$)$_3$CO-His-(D-1-Nal)-Arg-NHEt
Ph(CH$_2$)$_3$CO-His-(D-2-Nal)-Arg-NHEt
Ph(CH$_2$)$_3$CO-His-(D-4-Bip)-Arg-NHEt
Ph(CH$_2$)$_3$CO-His-(D-4-tBuPhe)-Arg-NHEt
4-FC$_6$H$_4$CH$_2$CO-His-(D-Phe)-Arg-NHEt
4-FC6H4CH2CO-His-(D-4-FPhe)-Arg-NHEt
4-FC$_6$H$_4$CH$_2$CO-His-(D-1-Nal)-Arg-NHEt
4-FC$_6$H$_4$CH$_2$CO-His-(D-2-Nal)-Arg-NHEt
4-FC$_6$H$_4$CH$_2$CO-His-(D-4-Bip)-Arg-NHEt
4-FC$_6$H$_4$CH$_2$CO-His-(D-4-tBuPhe)-Arg-NHEt Example 9

Formulation

An exemplary topical pharmaceutical composition is formulated as follows:

| Ingredient | Amount |
|---|---|
| LK-511 | 40 mg/ml |
| Propylene glycol | 35% (v/v) |
| Water | 65% (v/v) |
| 10 mM citric acid | Adjust pH to 4.0 |

What is claimed is:

1. A method of treating a skin disorder comprising administering to an individual in need thereof a therapeutic amount of a composition comprising:
   (a) a peptide agonist that binds human melanocortin 1 receptor (MC1R) selected from the group consisting of:
   Ph(CH$_2$)$_3$CO-His-(D-1-Nal)-Arg-Trp-NH$_2$;
   Ph(CH$_2$)$_3$CO-His-(D-4-Bip)-Arg-NH$_2$;
   Ph(CH$_2$)$_3$CO-His-(D-4-Bip)-Arg-NHMe;
   Ph(CH$_2$)$_3$CO-His-(D-4-tBuPhe)-Arg-NH$_2$; and
   (b) one or more pharmaceutically-acceptable excipients, wherein the administering delivers the peptide agonist to melanocytes in the skin.

2. The method of claim 1, wherein the skin disorder is selected from the group consisting of melanoma, basal cell carcinoma, squamous cell carcinoma, porphyria, polymorphous light eruption, vitiligo, and solar urticaria.

3. The method of claim 1, wherein the skin disorder is associated with a loss-of-function allelic variant of melanocortin 1 receptor (MC1R) gene.

4. The method of claim 1, wherein the skin disorder is associated with a mutation of a predisposition gene selected from the group consisting of p16, p14 ARF, and CDK4.

5. The method of claim 1, wherein the skin disorder is a disorder that benefits from agonism of melanocortin 1 receptor (MC1R).

6. The method of claim 1, wherein the peptide agonist stimulates production of melanin by melanocytes, thereby providing increased skin protection from ultraviolet radiation.

7. The method of claim 1, wherein the peptide agonist activates DNA repair pathways.

8. The method of claim 1, wherein administering comprises topical or systemic administration.

9. The method of claim 1, further comprising administering a sunscreen.

10. The method of claim 1, wherein the peptide agonist that binds human MC1R is Ph(CH$_2$)$_3$CO-His-(D-1-Nal)-Arg-Trp-NH$_2$.

11. The method of claim 1, wherein the peptide agonist that binds human MC1R is Ph(CH$_2$)$_3$CO-His-(D-4-Bip)-Arg-NH$_2$.

12. The method of claim 1, wherein the peptide agonist that binds human MC1R is Ph(CH$_2$)$_3$CO-His-(D-4-Bip)-Arg-NHMe.

13. The method of claim 1, wherein the peptide agonist that binds human MC1R is Ph(CH$_2$)$_3$CO-His-(D-4-tBuPhe)-Arg-NH$_2$.

* * * * *

UNITED STATES PATENT AND TRADEMARK OFFICE
CERTIFICATE OF CORRECTION

PATENT NO. : 10,301,355 B2
APPLICATION NO. : 15/794301
DATED : May 28, 2019
INVENTOR(S) : Zalfa A. Abdel-Malek, Leonid Koikov and James J. Knittel It is certified that error appears in the above-identified patent and that said Letters Patent is hereby corrected as shown below:

In the Specification

On Column 1 under the heading FEDERALLY SPONSORED RESEARCH OR DEVELOPMENT, please replace the paragraph with the following:
This invention was made with government support under CA114095 awarded by National Institutes of Health. The government has certain rights in the invention.

Signed and Sealed this
Twenty-fourth Day of December, 2019

Andrei Iancu
*Director of the United States Patent and Trademark Office*